United States Patent
Zhong et al.

(10) Patent No.: US 11,293,059 B2
(45) Date of Patent: Apr. 5, 2022

(54) MESYLATE BASED MASTER MIX

(71) Applicant: LIFE TECHNOLOGIES CORPORATION, Carlsbad, CA (US)

(72) Inventors: Chang Zhong, Foster City, CA (US); Julio Mulero, Carlsbad, CA (US); Steven Menchen, Fremont, CA (US)

(73) Assignee: LIFE TECHNOLOGIES CORPORATION, Carlsbad, CA (US)

(*) Notice: Subject to any disclaimer, the term of this patent is extended or adjusted under 35 U.S.C. 154(b) by 112 days.

(21) Appl. No.: 16/623,975

(22) PCT Filed: Jun. 20, 2018

(86) PCT No.: PCT/US2018/038531
§ 371 (c)(1),
(2) Date: Dec. 18, 2019

(87) PCT Pub. No.: WO2018/237024
PCT Pub. Date: Dec. 27, 2018

(65) Prior Publication Data
US 2020/0199652 A1 Jun. 25, 2020

Related U.S. Application Data

(60) Provisional application No. 62/523,736, filed on Jun. 22, 2017.

(51) Int. Cl.
C12Q 1/686 (2018.01)
C12Q 1/6848 (2018.01)

(52) U.S. Cl.
CPC .......... *C12Q 1/686* (2013.01); *C12Q 1/6848* (2013.01); *C12Q 2527/125* (2013.01)

(58) Field of Classification Search
None
See application file for complete search history.

(56) References Cited

U.S. PATENT DOCUMENTS

| 5,906,819 A | * | 5/1999 | Kaibuchi | C07K 14/4703 424/94.5 |
| 2004/0023207 A1 | * | 2/2004 | Polansky | A61K 48/005 435/5 |
| 2005/0266458 A1 | * | 12/2005 | Andersen | C12Q 1/68 435/6.14 |
| 2016/0264950 A1 | * | 9/2016 | Rogers | C12N 9/99 |
| 2016/0265068 A1 | * | 9/2016 | Hayden | C12Q 1/6846 |

FOREIGN PATENT DOCUMENTS

| WO | WO-2012138416 | 10/2012 |
| WO | WO-2016103034 | 6/2016 |

OTHER PUBLICATIONS

Nunoki et al. Activation of purified calcium channels by stoichiometric protein phosphorylation. Proc. Natl.Acad. Sci. USA 86:6816-6820. (Year: 1989).*
Cease et al., "Optimized PCR Using Vent Polymerase", Genome Research, vol. 3, No. 5, Mar. 1994, pp. 298-300.
Lorkovicacute, "The Influence of Ionic Strength on Potassium Contractures and Calcium Movements in Frog Muscle", Journal of General Physiology, vol. 50, No. 4, Mar. 1967, pp. 883-891.
Nagai et al., "Additive Effects of Bovine Serum Albumin, Dithiothreitol, and Glycerol on PCR", Biochemistry and Molecular Biology International, vol. 44, No. 1, Jan. 1998, pp. 157-163.
Palfrey et al., "Simplified preparation of human arterial sections for PCR analysis of Chlamydia pneumoniae and human DNA", Molecular Pathology, vol. 52, No. 5, Oct. 1999, pp. 289-294.
PCT/US2018/038531, Search Report and Written Opinion, dated Aug. 21, 2018, 12 pages.

* cited by examiner

*Primary Examiner* — Samuel C Woolwine
(74) *Attorney, Agent, or Firm* — Workman Nydegger

(57) ABSTRACT

Disclosed herein are mesylate containing compositions, methods of use of such compositions and kits of components encompassing such compositions for improving the amplification of nucleic acids, especially in the presence of enzymatic inhibitors. These find particular use in forensic and environmental analyses. The instant disclosure provides new compositions, methods and kits of components for overcoming PCR inhibition. In some embodiments disclosed herein is a PCR master mix, the PCR master mix encompassing a mesylate.

31 Claims, 14 Drawing Sheets

MESYLATE BASED MASTER MIX

CROSS-REFERENCE

This application is a 371 U.S. National Phase of PCT Application No. PCT/US2018/038531 filed Jun. 20, 2018, which application claims the benefit under 35 U.S.C. § 119(e) of U.S. Provisional Application No. 62/523,736 filed Jun. 22, 2017. The entire contents of the aforementioned applications are incorporated by reference herein.

FIELD

Disclosed herein are mesylate containing compositions, methods of use of such compositions and kits of components encompassing such compositions for improving the amplification of nucleic acids, especially in the presence of enzymatic inhibitors.

BACKGROUND

PCR inhibitors are factors that prevent the amplification of nucleic acids through the polymerase chain reaction (PCR). PCR inhibition is a cause of amplification failure when sufficient copies of DNA are present. PCR inhibitors usually affect PCR through interaction with DNA or interference with the DNA polymerase.

A common problem in forensic genetic analysis is the presence of PCR inhibitors. These interfering substances present a challenge for forensic human identification due to inhibitory effects on the amplification of short tandem repeats. The overall result can be no amplified product or only partial amplifications.

Disclosed herein are compositions, methods and kits for overcoming PCR inhibition, particularly in forensic analysis.

BRIEF SUMMARY

For as long as scientists have used the polymerase chain reaction (PCR), PCR inhibitors have been obstacles to success. Materials encountered in forensic investigations, such as blood, fabrics, tissues and soil, inherently contain PCR inhibitors. The instant disclosure provides new compositions, methods and kits of components for overcoming such PCR inhibition.

In some embodiments disclosed herein is a PCR master mix, the PCR master mix encompassing a mesylate.

In some embodiments a kit of components is disclosed, the kit of components encompassing a vessel containing a PCR master mix, the PCR master mix encompassing a mesylate.

In some embodiments, methods are disclosed the methods encompassing contacting a sample with a composition, thereby forming a contacted composition, the composition encompassing a biological buffer, a mesylate, a proteinaceous compound, a stabilizer compound, deoxynucleoside triphosphates, at least two primers and a polymerase, subjecting the contacted composition to thermal cycling protocol, thereby forming a cycled contacted composition and subjecting the cycled contacted composition to electrophoretic separation.

Further embodiments may be found in the following clauses.

1. A PCR master mix comprising a mesylate.
2. The PCR master mix of clause 1, further comprising a stabilizer compound.
3. The PCR master mix of clause 2, wherein the stabilizer compound comprises glycerol or sucrose.
4. The PCR master mix of clause 1, further comprising a proteinaceous compound.
5. The PCR master mix of clause 4, wherein the proteinaceous compound is bovine serum albumin.
6. The PCR master mix of clause 1, further comprising deoxynucleoside triphosphate.
7. The PCR master mix of clause 1, further comprising a DNA polymerase.
8. The PCR master mix of clause 1, wherein the mesylate is potassium methanesulfonate.
9. The PCR master mix of clause 1 comprising: Tris-mesylate (10-50 mM), potassium methanesulfonate (30-80 mM), bovine serum albumin (1.2-4 mg/ml) and glycerol (3-8% volume).
10. The PCR master mix of clause 9, further comprising a deoxynucleoside triphosphate, a non-ionic detergent and a DNA polymerase.
11. A kit comprising a first capped tube comprising a master mix, the master mix comprising a mesylate and a second capped tube comprising a primer.
12. The kit of clause 11, wherein the master mix further comprises a proteinaceous compound.
13. The kit of clause 11, wherein the master mix further comprises a polymerase.
14. The kit of clause 13, further comprising a third capped tube comprising an allelic ladder.
15. A method, the method comprising contacting a sample with a PCR master mix and thereby forming a contacted sample, the PCR master mix comprising Tris-mesylate (10-50 mM), potassium methanesulfonate (30-80 mM), bovine serum albumin (1.2-4 mg/ml), glycerol (3-8% volume), $MgSO_4$ (1.4-2.4 mM), Sodium Azide (0.01-0.04%), dATP, dCTP, dGTP, dTTP, at least two primers and a DNA polymerase, subjecting the contacted sample to a thermocycling protocol, thereby forming a cycled sample and subjecting the cycled sample to an electrophoretic separation and thereby detecting a presence or absence of an amplicon.

These and other embodiments will be described in more detail below.

BRIEF DESCRIPTION OF THE DRAWINGS

The skilled artisan will understand that the drawings described below are for illustration purposes only. The drawings are not intended to limit the scope of the present teachings in any way.

FIGS. 1A, 1C, 1E, 1G, and 1I illustrate result from a master mix without mesylate, and FIGS. 1B, 1D, 1F, 1H, and 1J illustrate results from a mesylate containing master mix. As can be seen, the number of resolved amplicons is greater when a mesylate is present in the PCR master mix relative to a PCR master mix lacking a mesylate.

In FIG. 3A, on the x-axis, from left the right, is variation of potassium methanesulfate over the range of 30-80 mM, magnesium methanosulfate over the range of 1.2-1.8 mM, and total deoxynucleoside triphosphates (dATP, dCTP, dGTP and dTTP) over the range of 600-1000 mM. A "desirability" index is right most. On the y-axis, from top to bottom, is the percent stutter observed for the short tandem repeat D13 locus and just below the same for the D22 locus. Stutter is an artefact observed when highly repetitive sequences, such as short tandem repeats, are amplified by PCR. Below stutter, the number of alleles (distinct amplicons) observed for each condition are indicated. A "desirability" index is bottom most. In FIG. 3B, on the x-axis, from left the right, is variation of Tween® 20 (poysorbate 20) over the range of 0.2-0.6%, Taq polymerase over the range of 0.2-0.6 units/µl, and bovine serum albumin over the range of 3-6 mg/ml. A "desirability" index is right most. On the y-axis, from top to bottom, the number of alleles (distinct amplicons) observed for each condition are indicated. A "desirability" index is bottom most.

DESCRIPTION OF EXEMPLARY EMBODIMENTS

Figure 1A:
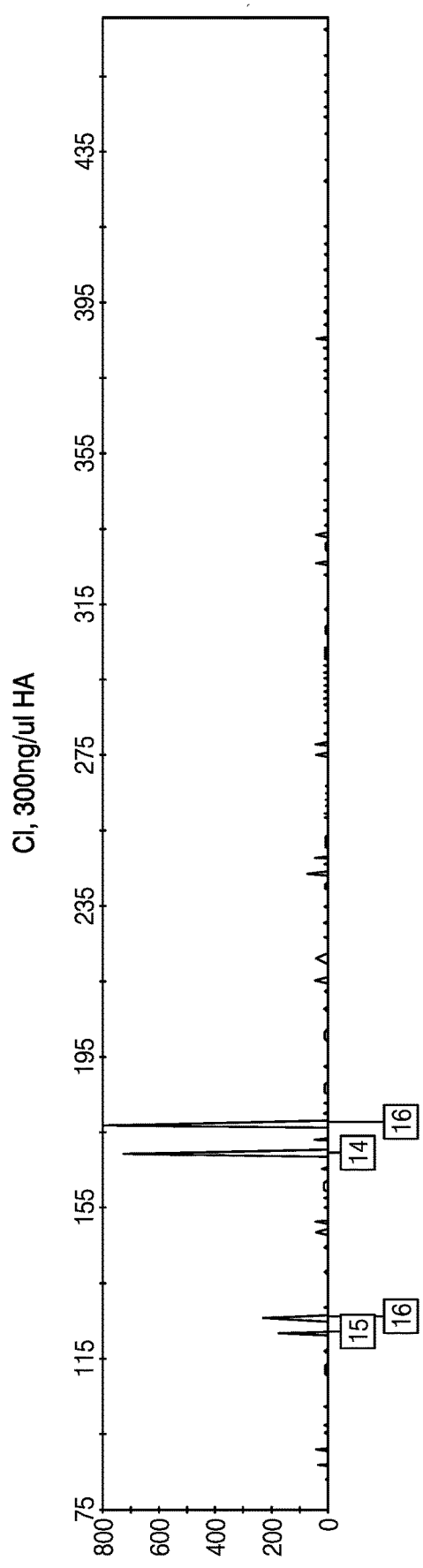
FIGS. 1A-1J. Electropherograms from capillary electrophoretic separation of amplicons resulting from PCR in the presence of the inhibitor humic acid.
Figure 1B:
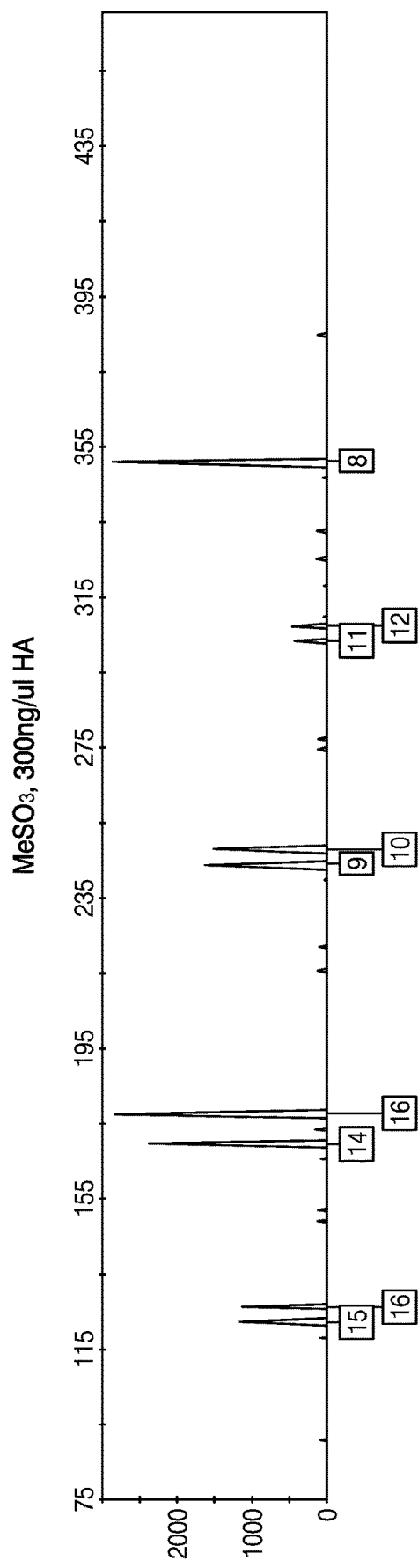
Figure 1C:
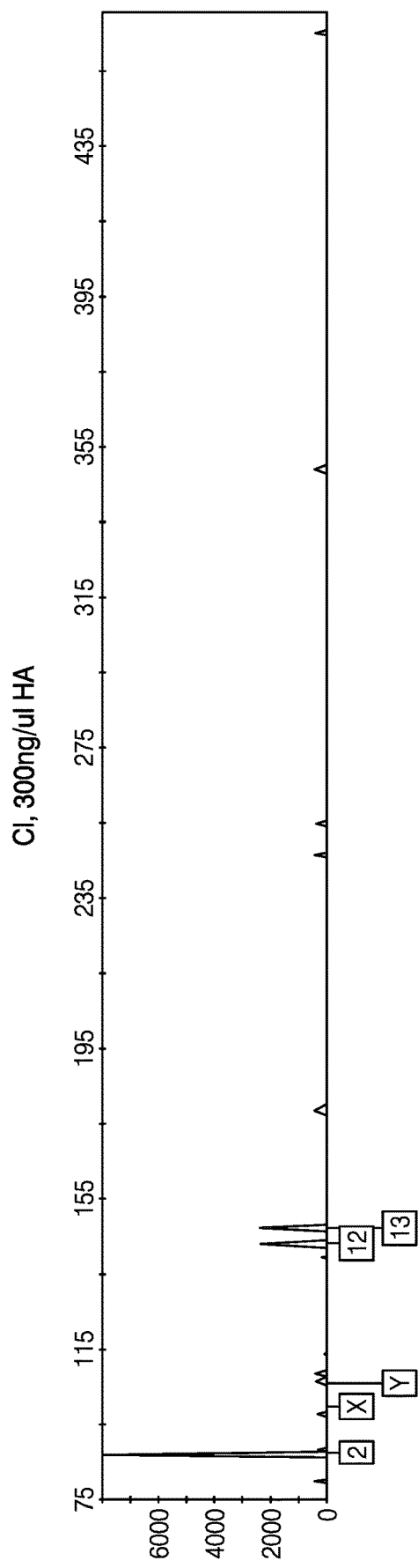
Figure 1D:
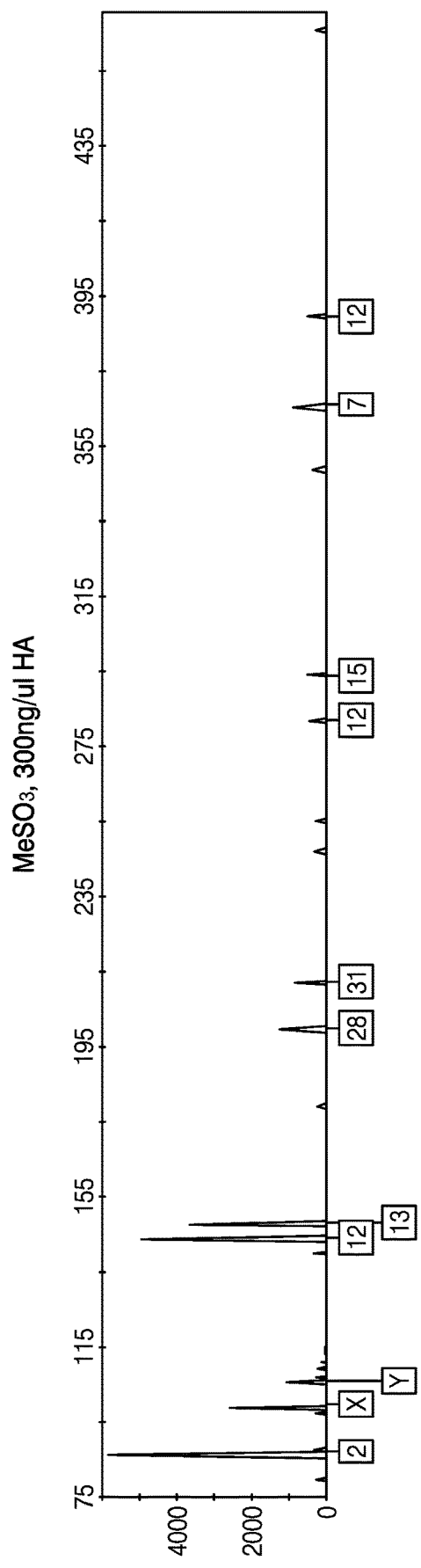
Figure 1E:
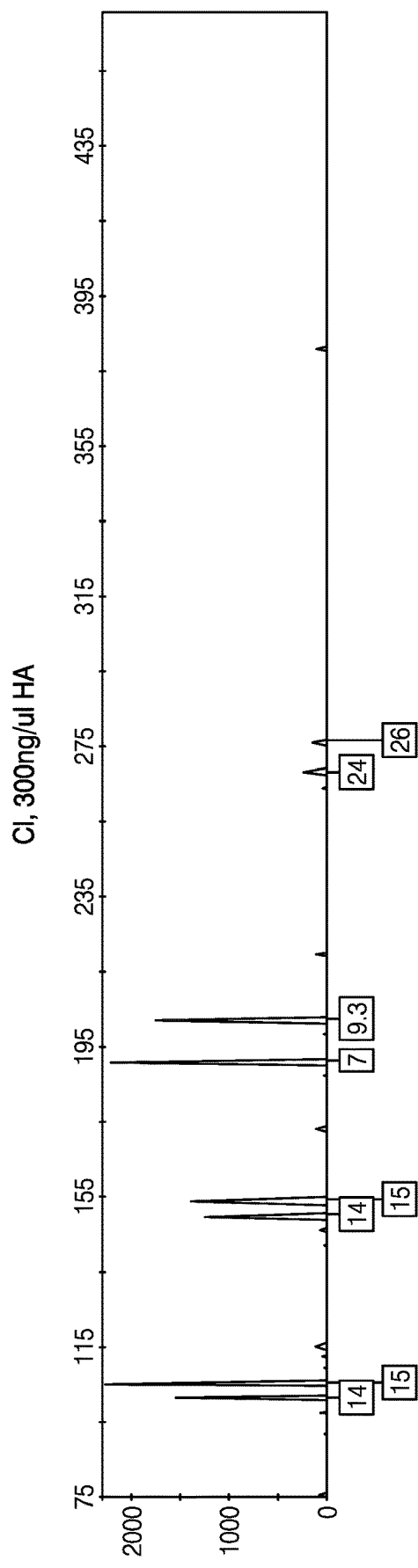
Figure 1F:
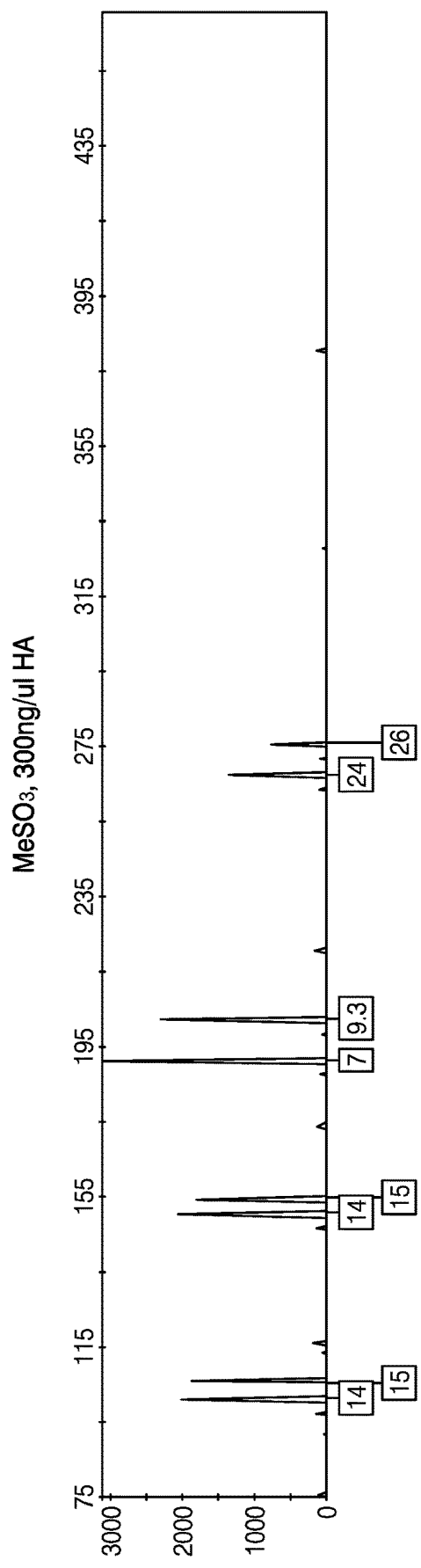
Figure 1G:
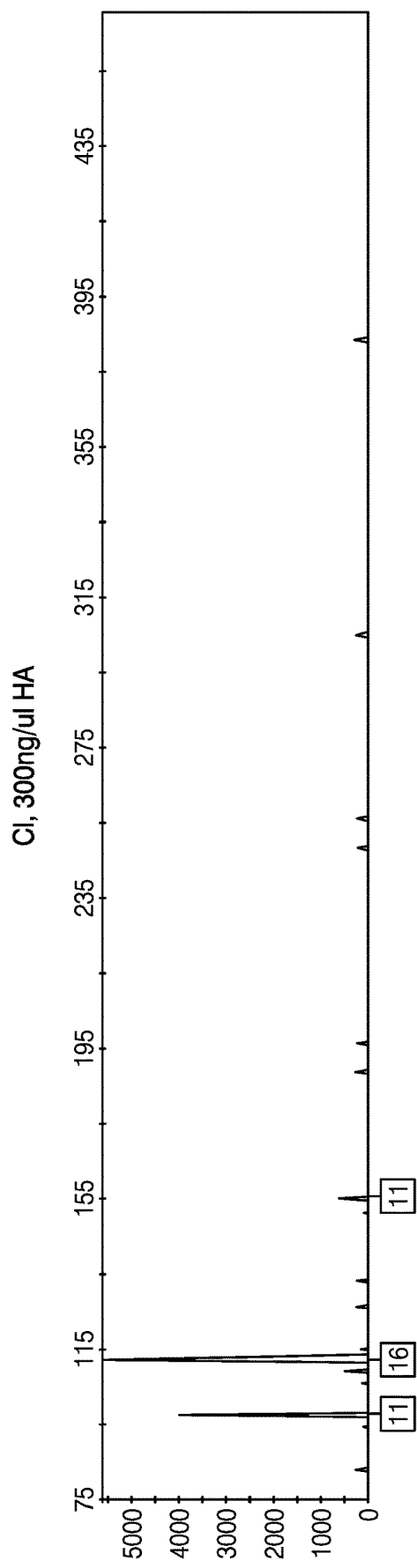
Figure 1H:
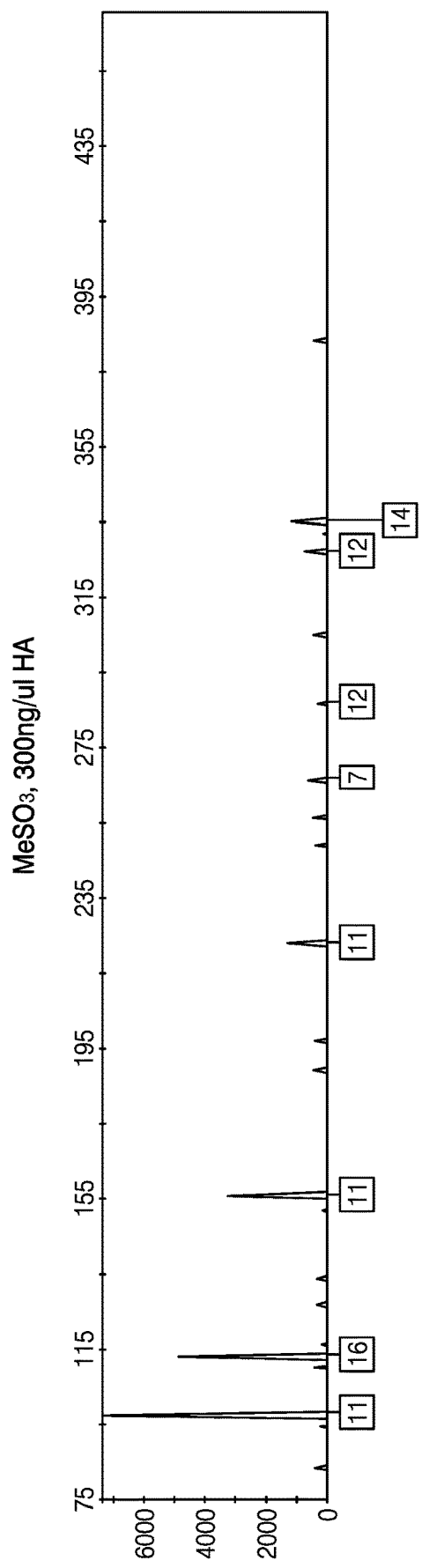
Figure 1I:
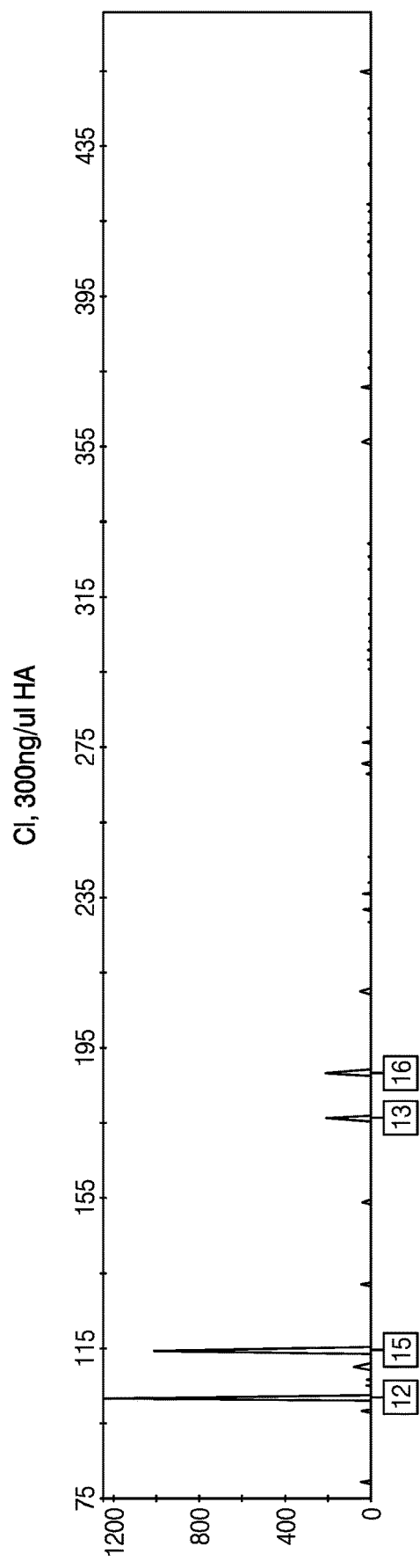
Figure 1J:
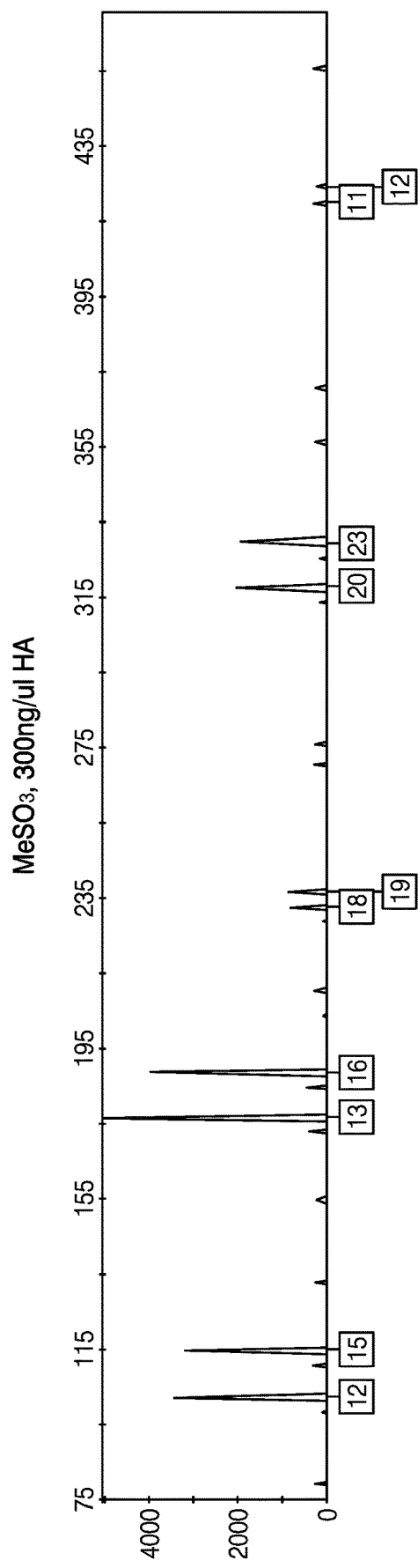

In the last few decades, the polymerase chain reaction (PCR) has become one of the most powerful molecular biology tools. PCR can be used for diagnosis of infectious or hereditary diseases and for genetic analyses generally. PCR is an enzymatic reaction and as such sensitive to inhibitors.

Most PCR inhibitors are organic compounds, for example, bile salts, urea, phenol, ethanol, polysaccharides, humic acids, tannic acid, melanin, collagen, myoglobulin, hemaglobulin, lactoferrin, immunoglobulin G, and proteases.

PCR inhibitors can be found in a variety of materials (organs, blood, and other body fluids), in the environment (water and soil) and food (meat, milk, fruits, vegetables and seafood).

PCR inhibitors are routinely found associated with nucleic acids isolated during forensic investigations and environmental studies. Humic acids, a series of substances produced during the decay process in soil, water and recent sediments, are often found in samples of forensic interest.

To overcome PCR inhibitors present in samples, the instant disclosure provides compositions.

Compositions

To overcome the effects of PCR inhibitors a composition is disclosed herein, the composition is a PCR master mix encompassing a mesylate. A "PCR master mix" is a composition whose components include a biological buffer and will be used for nucleic acid amplification using polymerase chain reaction. A master mix is often provided as a concentrate to be diluted to a working concentration by the user. When referencing concentrations of components in a PCR master mix herein, the concentration provided is the final working concentration of the component.

A "mesylate," also referred to as a methanesulfonate or mesilate, has the general formula $CH_3SO_3^-$. In some embodiments disclosed herein the mesylate is a potassium methanesulfonate [$CH_3KO_3S$; CAS No. 2386-56-3]. In other embodiments, the mesylate is a magnesium methanosulfonate [$C_2H_6MgO_6S_2$; CAS No. 62512-01]. In further embodiments, the mesylate is Tris-mesylate. Thus, in some embodiments the PCR master mix encompasses potassium methanesulfonate. In other embodiments, the PCR master mix encompasses magnesium methanosulfonate or magnesium sulfate.

In some embodiments, the potassium methanesulfonate is present in the PCR master mix at 30-80 mM. In other embodiments, the potassium methanesulfonate is present in the PCR master mix at 35 mM, 40 mM, 45 mM, 50 mM, 55 mM, 60 mM, 65 mM, 70 mM, or 75 mM.

In other embodiments, the magnesium methanosulfonate or magnesium sulfate is present in the PCR master mix at 1.2-1.8 mM. In other embodiments, the magnesium methanosulfonate is present at about 1.3 mM, 1.4 mM, 1.5 mM, 1.6 mM, or 1.7 mM.

A component of the PCR master mix is a biological buffer. A "biological buffer" is a solution with a pKa of between pH 5 and 9, water soluble, and wherein complexes formed with cations remain soluble generally. Examples of biological buffers are solutions of MES, Bis-Tris, ADA, PIPES, ACES, MOPSO, Bis-HCl Propane, BES, MOPS, DIPSO, TAPSO, Trizma® (Tris-HCl base), POPSO, HEPPS, TRICINE, Gly-Gly, Bicine, HEPBS, and TAPS. In some embodiments, the biological buffer has a pH of about 7.0. In some embodiments, the biological buffer has a pH of about 8.0. In other embodiments, the biological buffer has a pH of about 9.0. In some embodiments, the biological buffer has a pH of about 8.3.

The biological buffer in some embodiments is a solution of Tris-mesylate [($NH_2C(CH_2OH)3$.methanesulfonic acid)]. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the Tris-mesylate has a pH of about 8.3. One skilled in the art will understand that Tris-mesylate may be replaced in various embodiments with mesylate salts of the biological buffers listed above.

In some embodiments the PCR master mix encompasses potassium methanesulfonate and Tris-mesylate. In other embodiments the PCR master mix encompasses potassium methanesulfonate and Tris-mesylate, wherein the Tris-mesylate is at 10-50 mM. In other embodiments, the Tris-mesylate is present in the PCR master mix at 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In other embodiments, the Tris-mesylate has a pH of about 8.3.

In some embodiments the PCR master mix encompasses Tris-mesylate (10-50 mM) and potassium methanesulfonate (30-80 mM). In some embodiments, the Tris-mesylate is at about 10 mM, 15 mM, 20 mM, 25 mM, 30 mM, 35 mM, 40 mM, or 45 mM. In other embodiments, the potassium methanesulfonate is present at about 35 mM, 40 mM, 45 mM, 50 mM, 55 mM, 60 mM, 65 mM, 70 mM, or 75 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the Tris-mesylate has a pH of about 8.3.

In some embodiments, the PCR master mix encompasses Tris-mesylate (30 mM, pH 8.3) and potassium methanesulfonate (30 mM).

In some embodiments, the PCR master mix encompasses magnesium methanosulfonate and Tris-mesylate. In other embodiments the PCR master mix encompasses magnesium methanosulfonate and Tris-mesylate, wherein the Tris-mesylate is at 10-50 mM. In other embodiments, the Tris-mesylate is present in the PCR master mix at 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the Tris-mesylate has a pH of about 8.3.

In some embodiments, the PCR master mix encompasses Tris-mesylate (10-50 mM) and magnesium methanosulfonate (1.2-1.8 mM). In some embodiments, the Tris-mesylate is at about 10 mM, 15 mM, 20 mM, 25 mM, 30 mM, 35 mM, 40 mM, or 45 mM. In other embodiments, the magnesium methanosulfonate is present at about 1.3 mM, 1.4 mM, 1.5 mM, 1.6 mM, or 1.7 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the Tris-mesylate has a pH of about 8.3.

In some embodiments, PCR master mix encompasses a mesylate and a proteinaceous compound. A "proteinaceous compound" is a protein whose function is to stabilize enzymatic activity, particularly polymerase activity. Examples of proteinaceous compounds include albumin and gelatin. In some instances the albumin is bovine serum albumin.

In some embodiments, the PCR master mix encompasses a mesylate and a proteinaceous compound, wherein the proteinaceous compound is an albumin. In some embodiments the albumin is present in the PCR master mix at 1.2-4 mg/ml. In some embodiments the albumin is present in the PCR master mix at 1.5, 2, 2.5, 3, or 3.5 mg/ml. In some embodiments the albumin is bovine serum albumin. In some embodiments the bovine serum albumin is present in the PCR master mix at 1.2-4 mg/ml. In some embodiments the bovine serum albumin is present in the PCR master mix at 1.5, 2, 2.5, 3, or 3.5 mg/ml.

In some embodiments, the PCR master mix encompasses Tris-mesylate, a mesylate and a proteinaceous compound, wherein the proteinaceous compound is albumin. In some embodiments the albumin is present in the PCR master mix at 1.2-4 mg/ml. In some embodiments the albumin is present in the PCR master mix at 1.5, 2, 2.5, 3, or 3.5 mg/ml. In some embodiments the Tris-mesylate is present in the PCR master mix at 10-50 mM. In other embodiments, the Tris-mesylate s present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the Tris-mesylate has a pH of about 8.3.

In some embodiments, the PCR master mix encompasses Tris-mesylate, a mesylate and a proteinaceous compound, wherein the methanosulfate salt is potassium methanesulfonate and the proteinaceous compound is albumin. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the Tris-mesylate has a pH of about 8.3. In some embodiments the albumin is present in the PCR master mix at 1.2-4 mg/ml. In some embodiments the albumin is present in the PCR master mix at 1.5, 2, 2.5, 3, or 3.5 mg/ml. In some embodiments the PCR master mix encompasses Tris-mesylate (10-50 mM) and potassium methanesulfonate (30-80 mM). In other embodiments, the potassium methanesulfonate is present at about 35 mM, 40 mM, 45 mM, 50 mM, 55 mM, 60 mM, 65 mM, 70 mM, or 75 mM.

In some embodiments, the PCR master mix encompasses a mesylate and a proteinaceous compound, wherein the proteinaceous compound is bovine serum albumin. In some embodiments the bovine serum albumin is present in the PCR master mix at 1.2-4 mg/ml. In some embodiments the bovine serum albumin is present in the PCR master mix at 1.5, 2, 2.5, 3, or 3.5 mg/ml.

In some embodiments, the PCR master mix encompasses Tris-mesylate, a mesylate and a proteinaceous compound, wherein the proteinaceous compound is bovine serum albumin. In some embodiments the bovine serum albumin is present in the PCR master mix at 1.2-4 mg/ml. In some embodiments the bovine serum albumin is present in the PCR master mix at 1.5, 2, 2.5, 3, or 3.5 mg/ml. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the Tris-mesylate has a pH of about 8.3.

In some embodiments, the PCR master mix encompasses Tris-mesylate, a mesylate and a proteinaceous compound, wherein the mesylate is potassium methanesulfonate and the proteinaceous compound is bovine serum albumin. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the Tris-mesylate has a pH of about 8.3. In some embodiments the bovine serum albumin is present in the PCR master mix at 1.2-4 mg/ml. In some embodiments the bovine serum albumin is present in the PCR master mix at 1.5, 2, 2.5, 3, or 3.5 mg/ml. In some embodiments, the potassium methanesulfonate is present at 30-80 mM. In other embodiments, the potassium methanesulfonate is present at about 35 mM, 40 mM, 45 mM, 50 mM, 55 mM, 60 mM, 65 mM, 70 mM, or 75 mM.

In some embodiments, the PCR master mix encompasses Tris-mesylate (30 mM, pH 8.3), potassium methanesulfonate (35 mM) and bovine serum albumin (4 mg/ml).

In some embodiments, the PCR master mix encompasses Tris-mesylate, a mesylate and a proteinaceous compound, wherein the proteinaceous compound is gelatin. In some embodiments the gelatin is present in the PCR master mix at 1.2-4 mg/ml. In some embodiments the gelatin is present in the PCR master mix at 1.5, 2, 2.5, 3, or 3.5 mg/ml. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the Tris-mesylate has a pH of about 8.3.

In some embodiments, the PCR master mix encompasses Tris-mesylate, a mesylate and a proteinaceous compound, wherein the methanosulfate salt is potassium methanesulfonate and the proteinaceous compound is gelatin. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the Tris-mesylate has a pH of about 8.3. In some embodiments the gelatin is present in the PCR master mix at 1.2-4 mg/ml. In some embodiments the bovine serum albumin is present in the PCR master mix at 1.5, 2, 2.5, 3, or 3.5 mg/ml. In some embodiments the potassium methanesulfonate is 30-80 mM. In other embodiments, the potassium methanesulfonate is present at about 35 mM, 40 mM, 45 mM, 50 mM, 55 mM, 60 mM, 65 mM, 70 mM, or 75 mM.

In some embodiments, the PCR master mix encompasses Tris-mesylate, a mesylate and a proteinaceous compound, wherein the mesylate is magnesium methanosulfonate and the proteinaceous compound is bovine serum albumin. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the Tris-mesylate has a pH of about 8.3. In some embodiments the bovine serum albumin is present in the PCR master mix at 1.2-4 mg/ml. In some embodiments the bovine serum albumin is present in the PCR master mix at 1.5, 2, 2.5, 3, or 3.5 mg/ml. In some embodiments, the magnesium methanosulfonate is present at 1.2-1.8 mM. In other embodiments, the magnesium methanosulfonate is present at 35 mM, 40 mM, 45 mM, 50 mM, 55 mM, 60 mM, 65 mM, 70 mM, or 75 mM.

In some embodiments, the PCR master mix encompasses Tris-mesylate, a mesylate and a proteinaceous compound, wherein the mesylate is magnesium methanosulfonate and the proteinaceous compound is gelatin. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the Tris-mesylate has a pH of about 8.3. In some embodiments the gelatin is present in the PCR master mix at 1.2-4 mg/ml. In some embodiments the bovine serum albumin is present in the PCR master mix at 1.5, 2, 2.5, 3, or 3.5 mg/ml. In some embodiments, the magnesium methanosulfonate is present at 1.2-1.8 mM. In other embodiments, the magnesium methanosulfonate is present at 35 mM, 40 mM, 45 mM, 50 mM, 55 mM, 60 mM, 65 mM, 70 mM, or 75 mM.

In other embodiments, the PCR master mix encompasses a mesylate and a stabilizer compound. A "stabilizer compound" prevents freezing of an enzyme containing solution stored at a temperature of −20° C. while maintaining enzyme activity, as measured by enzymatic activity assay, relative to an enzyme solution stored at −20° C. without the stabilizer compound. Examples of a stabilizer compound are: glycerol and sucrose.

In some embodiments, the PCR master mix encompasses a mesylate and a stabilizer compound, wherein the stabilizer compound is glycerol. In other embodiments, the stabilizer compound is sucrose.

In some embodiments, the PCR master mix encompasses a mesylate and a stabilizer compound, wherein the stabilizer compound is glycerol. In some embodiments the glycerol is present in the PCR master mix at 3-8%. In some embodiments the glycerol is present in the PCR master mix at 3.5, 4, 4.5, 5, 5.5, 6, 6.5, 7, or 7.5%.

In some embodiments, the PCR master mix encompasses Tris-mesylate, a mesylate and a stabilizer compound, wherein the stabilizer compound is glycerol. In some embodiments the glycerol is present in the PCR master mix at 3-8%. In some embodiments the glycerol is present in the PCR master mix at 3.5, 4, 4.5, 5, 5.5, 6, 6.5, 7, or 7.5%. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the Tris-mesylate has a pH of about 8.3.

In some embodiments, the PCR master mix encompasses Tris-mesylate, a mesylate and a stabilizer compound, wherein the mesylate is potassium methanesulfonate and the stabilizer compound is glycerol. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the Tris-mesylate has a pH of about 8.3. In some embodiments the glycerol is present in the PCR master mix at 3-8%. In some embodiments the glycerol is present in the PCR master mix at 3.5, 4, 4.5, 5, 5.5, 6, 6.5, 7, or 7.5%. In some embodiments the PCR master mix encompasses potassium methanesulfonate (30-80 mM). In other embodiments, the potassium methanesulfonate is present at about 35 mM, 40 mM, 45 mM, 50 mM, 55 mM, 60 mM, 65 mM, 70 mM, or 75 mM.

In some embodiments, the PCR master mix encompasses Tris-mesylate (30 mM, pH 8.3), potassium methanosulfate (35 mM) and glycerol 5%.

In some embodiments, the PCR master mix encompasses Tris-mesylate, a mesylate and a stabilizer compound, wherein the mesylate is magnesium methanosulfonate and the stabilizer compound is glycerol. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM. In some embodiments the glycerol is present in the PCR master mix at 3-8%. In some embodiments the glycerol is present in the PCR master mix at 3.5, 4, 4.5, 5, 5.5, 6, 6.5, 7, or 7.5%.

In some embodiments, the PCR master mix encompasses Tris-mesylate, a mesylate and a stabilizer compound, wherein the stabilizer compound is sucrose. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the Tris-mesylate has a pH of about 8.3.

In some embodiments, the PCR master mix encompasses Tris-mesylate, a mesylate and a stabilizer compound, wherein the mesylate is potassium methanesulfonate and the stabilizer compound is sucrose. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the Tris-mesylate has a pH of about 8.3. In some embodiments the PCR master mix encompasses potassium methanesulfonate (30-80 mM). In other embodiments, the potassium methanesulfonate is present at about 35 mM, 40 mM, 45 mM, 50 mM, 55 mM, 60 mM, 65 mM, 70 mM, or 75 mM.

In some embodiments, the PCR master mix encompasses Tris-mesylate, a mesylate and a stabilizer compound, wherein the mesylate is magnesium methanosulfonate and the stabilizer compound is sucrose. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM.

In some embodiments, the PCR master mix encompasses a mesylate, a proteinaceous compound and a stabilizer compound. In some embodiments, the PCR master mix encompasses Tris-mesylate, a mesylate, a proteinaceous compound and a stabilizer compound. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the PCR master mix encompasses a mesylate, a proteinaceous compound and a stabilizer compound wherein the mesylate is potassium methanesulfonate. In some embodiments, the potassium methanesulfonate is present from 30-80 mM. In other embodiments, the potassium methanesulfonate is present at about 35 mM, 40 mM, 45 mM, 50 mM, 55 mM, 60 mM, 65 mM, 70 mM, or 75 mM. In some embodiments, the mesylate is magnesium methanosulfate. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM. In some embodiments, the PCR master mix encompasses a mesylate, a proteinaceous compound and a stabilizer compound, wherein the proteinaceous compound is albumin. In some embodiments the albumin is present in the PCR master mix at 1.2-4 mg/ml. In some embodiments the albumin is present in the PCR master mix at 1.5, 2, 2.5, 3, or 3.5 mg/ml. In some instances the albumin is bovine serum albumin. In some embodiments the bovine serum albumin is present in the PCR master mix at 1.2-4 mg/ml. In some embodiments the bovine serum albumin is present in the PCR master mix at 1.5, 2, 2.5, 3, or 3.5 mg/ml. In some embodiments the proteinaceous compound is gelatin. In some embodiments, the PCR master mix encompasses a mesylate, a proteinaceous compound and a stabilizer compound, wherein the stabilizer compound is glycerol. In some embodiments the glycerol is present in the PCR master mix at 3-8%. In some embodiments the glycerol is present in the PCR master mix at 3.5, 4, 4.5, 5, 5.5, 6, 6.5, 7, or 7.5%. In other embodiments, the stabilizer compound is sucrose.

In some embodiments, the PCR master mix encompasses Tris-mesylate (30 mM, pH 8.3), potassium methanesulfonate (35 mM), bovine serum albumin (2 mg/m1) and glycerol (5%).

In some embodiments, the PCR master mix encompasses a mesylate and a non-ionic detergent. In some embodiments, the non-ionic detergent is present from 0.1-0.9%. In some embodiments the non-ionic detergent is polysorbate 20 [polyoxyethylene (20) sorbitan monolaurate]. Common commercial names for polysorbate 20 are: Tween® 20, Scattics and Alkest TW 20. In some embodiments, the polysorbate 20 is present from 0.1-0.9%. In some embodiments, the polysorbate 20 is present at 0.2%.

Accordingly, in some embodiments disclosed herein the PCR master mix encompasses Tris-mesylate, a mesylate, and a non-ionic detergent. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the PCR master mix encompasses a mesylate, wherein the mesylate is potassium methanesulfonate. In some embodiments, the potassium methanesulfonate is present from 30-80 mM. In other embodiments, the potassium methanesulfonate is present at about 35 mM, 40 mM, 45 mM, 50 mM, 55 mM, 60 mM, 65 mM, 70 mM, or 75 mM. In other embodiments, the mesylate is magnesium methanosulfate. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM. In some embodiments, the non-ionic detergent is present from 0.1-0.9%. In some embodiments the non-ionic detergent is polysorbate 20. In some embodiments, the polysorbate 20 is present from 0.1-0.9%. In some embodiments, the polysorbate 20 is present at 0.2%.

In some embodiments, the PCR master mix encompasses Tris-mesylate (30 mM; pH 8.3), potassium methanesulfate (35 mM), and polysorbate 20 (0.2%).

In some embodiments, the PCR master mix encompasses a mesylate, a proteinaceous compound and a non-ionic detergent. In some embodiments the biological buffer is Tris-mesylate and the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the PCR master mix encompasses a mesylate, a proteinaceous compound and a non-ionic detergent wherein the mesylate is potassium methanesulfonate. In some embodiments, the potassium methanesulfonate is present from 30-80 mM. In other embodiments, the potassium methanesulfonate is present at about 35 mM, 40 mM, 45 mM, 50 mM, 55 mM, 60 mM, 65 mM, 70 mM, or 75 mM. In some embodiments, the mesylate is magnesium methanosulfate. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM. In some embodiments, the PCR master mix encompasses a mesylate, a proteinaceous compound and a non-ionic detergent, wherein the proteinaceous compound is albumin. In some embodiments the albumin is present in the PCR master mix at 1.2-4 mg/ml. In some embodiments the albumin is present in the PCR master mix at 1.5, 2, 2.5, 3, or 3.5 mg/ml. In some instances the albumin is bovine serum albumin. In some embodiments the bovine serum albumin is present in the PCR master mix at 1.2-4 mg/ml. In some embodiments the bovine serum albumin is present in the PCR master mix at 1.5, 2, 2.5, 3, or 3.5 mg/ml. In some embodiments the proteinaceous compound is gelatin. In some embodiments, the PCR master mix encompasses a mesylate, a proteinaceous compound and a non-ionic detergent, wherein the non-ionic detergent is present from 0.1-0.9%. In some embodiments the non-ionic detergent is polysorbate 20. In some embodiments, the polysorbate 20 is present from 0.1-0.9%. In some embodiments, the polysorbate 20 is present at 0.2%.

In some embodiments, the PCR master mix encompasses Tris-mesylate (30 mM; pH 8.3), potassium methanesulfate (35 mM), bovine serum albumin (2 mg/ml) and polysorbate 20 (0.2%).

In some embodiments, the PCR master mix encompasses a mesylate, a stabilizer compound and a non-ionic detergent. In some embodiments, the PCR master mix encompasses Tris-mesylate, a mesylate, a stabilizer compound and a non-ionic detergent. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the PCR master mix encompasses a mesylate, a stabilizer compound and a non-ionic detergent wherein the mesylate is potassium methanesulfonate. In some embodiments, the potassium methanesulfonate is present from 30-80 mM. In other embodiments, the potassium methanesulfonate is present at about 35 mM, 40 mM, 45 mM, 50 mM, 55 mM, 60 mM, 65 mM, 70 mM, or 75 mM. In some embodiments, the mesylate is magnesium methanosulfate. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM. In some embodiments, the PCR master mix encompasses a mesylate, a stabilizer compound and a non-ionic detergent, wherein the stabilizer compound is glycerol. In some embodiments the glycerol is present in the PCR master mix at 3-8%. In some embodiments the glycerol is present in the PCR master mix at 3.5, 4, 4.5, 5, 5.5, 6, 6.5, 7, or 7.5%. In other embodiments, the stabilizer compound is sucrose. In some embodiments, the PCR master mix encompasses a mesylate, a stabilizer and a non-ionic detergent, wherein the non-ionic detergent is present from 0.1-0.9%. In some embodiments the non-ionic detergent is polysorbate 20. In some embodiments, the polysorbate 20 is present from 0.1-0.9%. In some embodiments, the polysorbate 20 is present at 0.2%.

In some embodiments, the PCR master mix encompasses Tris-mesylate (30 mM; pH 8.3), potassium methanesulfate (35 mM), glycerol (5%) and polysorbate 20 (0.2%).

In some embodiments, the PCR master mix encompasses a mesylate, a proteinaceous compound, a stabilizer compound and a non-ionic detergent. In some embodiments, the PCR master mix encompasses Tris-mesylate, a mesylate, a proteinaceous compound and a stabilizer compound. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the PCR master mix encompasses a mesylate, a proteinaceous compound and a stabilizer compound wherein the mesylate is potassium methanesulfonate. In some embodiments, the potassium methanesulfonate is present from 30-80 mM. In other embodiments, the potassium methanesulfonate is present at about 35 mM, 40 mM, 45 mM, 50 mM, 55 mM, 60 mM, 65 mM, 70 mM, or 75 mM. In some embodiments, the mesylate is magnesium methanosulfate. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM. In some embodiments, the PCR master mix encompasses a mesylate, a proteinaceous compound and a stabilizer compound, wherein the proteinaceous compound is albumin. In some embodiments the albumin is present in the PCR master mix at 1.2-4 mg/ml. In some embodiments the albumin is present in the PCR master mix at 1.5, 2, 2.5, 3, or 3.5 mg/ml. In some instances the albumin is bovine serum albumin. In some embodiments the bovine serum albumin is present in the PCR master mix at 1.2-4 mg/ml. In some embodiments the bovine serum albumin is present in the PCR master mix at 1.5, 2, 2.5, 3, or 3.5 mg/ml. In some embodiments the proteinaceous compound is gelatin. In some embodiments, the PCR master mix encompasses a mesylate, a proteinaceous compound and a stabilizer compound, wherein the stabilizer compound is glycerol. In some embodiments the glycerol is present in the PCR master mix at 3-8%. In some embodiments the glycerol is present in the PCR master mix at 3.5, 4, 4.5, 5, 5.5, 6, 6.5, 7, or 7.5%. In other embodiments, the stabilizer compound is sucrose. In some embodiments, the PCR master mix encompasses a mesylate, a proteinaceous compound, a stabilizer and a non-ionic detergent, wherein the non-ionic detergent is present from 0.1-0.9%. In some embodiments the non-ionic detergent is polysorbate 20. In some embodiments, the polysorbate 20 is present from 0.1-0.9%. In some embodiments, the polysorbate 20 is present at 0.2%.

In some embodiments, the PCR master mix encompasses Tris-mesylate (30 mM, pH 8.3), potassium methanesulfonate (35 mM), bovine serum albumin (2 mg/ml), glycerol (5%) and polysorbate 20 (0.2%).

In some embodiments, the PCR master mix encompasses a mesylate and magnesium sulfate ($MgSO_4$). In some embodiments, the magnesium sulfate is at 1.2-2.4 mM. In some embodiments the magnesium sulfate is at 1.6 mM.

In some embodiments disclosed herein the PCR master mix encompasses a biological buffer, a mesylate, and magnesium sulfate. In some embodiments the biological buffer is Tris-mesylate. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the PCR master mix encompasses a mesylate, wherein the mesylate is potassium methanesulfonate. In some embodiments, the potassium methanesulfonate is present from 30-80 mM. In other embodiments, the potassium methanesulfonate is present at about 35 mM, 40 mM, 45 mM, 50 mM, 55 mM, 60 mM, 65 mM, 70 mM, or 75 mM. In other embodiments, the mesylate is magnesium methanosulfate. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM. In some embodiments, the magnesium sulfate is at 1.2-2.4 mM. In some embodiments the magnesium sulfate is at 1.6 mM.

In some embodiments, the PCR master mix encompasses Tris-mesylate (30 mM; pH 8.3), potassium methanesulfate (35 mM), and magnesium sulfate (1.6 mM).

In some embodiments, the PCR master mix encompasses a mesylate, a proteinaceous compound and magnesium sulfate. In some embodiments the biological buffer is Tris-mesylate and the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the PCR master mix encompasses a mesylate, a proteinaceous compound and magnesium sulfate wherein the mesylate is potassium methanesulfonate. In some embodiments, the potassium methanesulfonate is present from 30-80 mM. In other embodiments, the potassium methanesulfonate is present at about 35 mM, 40 mM, 45 mM, 50 mM, 55 mM, 60 mM, 65 mM, 70 mM, or 75 mM. In some embodiments, the mesylate is magnesium methanosulfate. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM. In some embodiments, the PCR master mix encompasses a mesylate, a proteinaceous compound and magnesium sulfate, wherein the proteinaceous compound is albumin. In some embodiments the albumin is present in the PCR master mix at 1.2-4 mg/ml. In some embodiments the albumin is present in the PCR master mix at 1.5, 2, 2.5, 3, or 3.5 mg/ml. In some instances the albumin is bovine serum albumin. In some embodiments the bovine serum albumin is present in the PCR master mix at 1.2-4 mg/ml. In some embodiments the bovine serum albumin is present in the PCR master mix at 1.5, 2, 2.5, 3, or 3.5 mg/ml. In some embodiments the proteinaceous compound is gelatin. In some embodiments, the PCR master mix encompasses a mesylate, a proteinaceous compound and magnesium sulfate, wherein the magnesium sulfate is at 1.2-2.4 mM. In some embodiments the magnesium sulfate is at 1.6 mM.

In some embodiments, the PCR master mix encompasses Tris-mesylate (30 mM; pH 8.3), potassium methanesulfate (35 mM), bovine serum albumin (2 mg/ml) and magnesium sulfate (1.6 mM).

In some embodiments, the PCR master mix encompasses a mesylate, a stabilizer compound and magnesium sulfate. In some embodiments, the PCR master mix encompasses Tris-mesylate, a mesylate, a stabilizer compound and magnesium sulfate. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the PCR master mix encompasses a mesylate, a stabilizer compound and magnesium sulfate wherein the mesylate is potassium methanesulfonate. In some embodiments, the potassium methanesulfonate is present from 30-80 mM. In other embodiments, the potassium methanesulfonate is present at about 35 mM, 40 mM, 45 mM, 50 mM, 55 mM, 60 mM, 65 mM, 70 mM, or 75 mM. In some embodiments, the mesylate is magnesium methanosulfate. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM. In some embodiments, the PCR master mix encompasses a mesylate, a stabilizer compound and magnesium sulfate, wherein the stabilizer compound is glycerol. In some embodiments the glycerol is present in the PCR master mix at 3-8%. In some embodiments the glycerol is present in the PCR master mix at 3.5, 4, 4.5, 5, 5.5, 6, 6.5, 7, or 7.5%. In other embodiments, the stabilizer compound is sucrose. In some embodiments, the PCR master mix encompasses a mesylate, a stabilizer compound and magnesium sulfate, wherein the magnesium sulfate is at 1.2-2.4 mM. In some embodiments the magnesium sulfate is at 1.6 mM.

In some embodiments, the PCR master mix encompasses Tris-mesylate (30 mM; pH 8.3), potassium methanesulfate (35 mM), glycerol (5%) and magnesium sulfate (1.6 mM).

In some embodiments, the PCR master mix encompasses a mesylate, a non-ionic detergent, and magnesium sulfate. In some embodiments, the PCR master mix encompasses Tris-mesylate, a mesylate, a proteinaceous compound and a stabilizer compound. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the PCR master mix encompasses a mesylate, a proteinaceous compound and a stabilizer compound wherein the mesylate is potassium methanesulfonate. In some embodiments, the potassium methanesulfonate is present from 30-80 mM. In other embodiments, the potassium methanesulfonate is present at about 35 mM, 40 mM, 45 mM, 50 mM, 55 mM, 60 mM, 65 mM, 70 mM, or 75 mM. In some embodiments, the mesylate is magnesium methanosulfate. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM. In some embodiments, the PCR master mix encompasses a mesylate, a non-ionic detergent and magnesium sulfate, wherein the non-ionic detergent is present from 0.1-0.9%. In some embodiments the non-ionic detergent is polysorbate 20. In some embodiments, the polysorbate 20 is present from 0.1-0.9%. In some embodiments, the polysorbate 20 is present at 0.2%. In some embodiments, the PCR master mix encompasses a mesylate, a non-ionic detergent and magnesium sulfate, wherein the magnesium sulfate is at 1.2-2.4 mM. In some embodiments the magnesium sulfate is at 1.6 mM.

In some embodiments, the PCR master mix encompasses Tris-mesylate (30 mM, pH 8.3), potassium methanesulfonate (35 mM), polysorbate 20 (0.2%) and magnesium sulfate (1.6 mM).

In some embodiments, the PCR master mix encompasses a mesylate, a proteinaceous compound, a stabilizer compound, a non-ionic detergent and magnesium sulfate. In some embodiments, the PCR master mix encompasses Tris-mesylate, a mesylate, a proteinaceous compound, a stabilizer compound, a non-ionic detergent and magnesium sulfate. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the PCR master mix encompasses a mesylate, a proteinaceous compound, a stabilizer compound, a non-ionic detergent and magnesium sulfate wherein the mesylate is potassium methanesulfonate. In some embodiments, the potassium methanesulfonate is present from 30-80 mM. In other embodiments, the potassium methanesulfonate is present at about 35 mM, 40 mM, 45 mM, 50 mM, 55 mM, 60 mM, 65 mM, 70 mM, or 75 mM. In some embodiments, the mesylate is magnesium methanosulfate. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM. In some embodiments, the PCR master mix encompasses a mesylate, a proteinaceous compound, a stabilizer compound, a non-ionic detergent and magnesium sulfate, wherein the proteinaceous compound is albumin. In some embodiments the albumin is present in the PCR master mix at 1.2-4 mg/ml. In some embodiments the albumin is present in the PCR master mix at 1.5, 2, 2.5, 3, or 3.5 mg/ml. In some instances the albumin is bovine serum albumin. In some embodiments the bovine serum albumin is present in the PCR master mix at 1.2-4 mg/ml. In some embodiments the bovine serum albumin is present in the PCR master mix at 1.5, 2, 2.5, 3, or 3.5 mg/ml. In some embodiments, the proteinaceous compound is gelatin. In some embodiments, the PCR master mix encompasses a mesylate, a proteinaceous compound, a stabilizer compound, a non-ionic detergent and magnesium sulfate wherein the stabilizer compound is glycerol. In some embodiments the glycerol is present in the PCR master mix at 3-8%. In some embodiments the glycerol is present in the PCR master mix at 3.5, 4, 4.5, 5, 5.5, 6, 6.5, 7, or 7.5%. In other embodiments, the stabilizer compound is sucrose. In some embodiments, the PCR master mix encompasses a mesylate, a proteinaceous compound, a stabilizer compound, a non-ionic detergent and magnesium sulfate, wherein the non-ionic detergent is present from 0.1-0.9%. In some embodiments the non-ionic detergent is polysorbate 20. In some embodiments, the polysorbate 20 is present from 0.1-0.9%. In some embodiments, the polysorbate 20 is present at 0.2%. In some embodiments, the PCR master mix encompasses a mesylate, a proteinaceous compound, a stabilizer compound, a non-ionic detergent and magnesium sulfate, wherein the magnesium sulfate is at 1.2-2.4 mM. In some embodiments the magnesium sulfate is at 1.6 mM.

In some embodiments, the PCR master mix encompasses Tris-mesylate (30 mM, pH 8.3), potassium methanesulfonate (35 mM), bovine serum albumin (2 mg/ml), glycerol (5%), polysorbate 20 (0.2%) and magnesium sulfate (1.6 mM).

In some embodiments, the PCR master mix disclosed herein further encompasses a polymerase. A "polymerase" is an enzyme that catalyzes the polymerization of nucleosides. A DNA polymerase catalyzes the polymerization of deoxynucleosides such as the deoxynucleoside triphosphates adenosine, cytidine, guanosine, and thymidine.

Examples of DNA polymerases include *Pyrococcus furiosus* (Pfu) DNA polymerase, *E. coli* DNA polymerase I, T7 DNA polymerase, *Thermus thermophilus* (Tth) DNA polymerase, *Bacillus stearothermophilus* DNA polymerase, *Thermococcus litoralis* (Tli) DNA polymerase (also referred to as Vent DNA polymerase), *Thermotoga maritima* (Tma) DNA polymerase, *Thermus aquaticus* (Taq) DNA polymerase, *Pyrococcus kodakaraensis* KOD DNA polymerase, and *Pyrococcus* GB-D (PGB-D) DNA polymerase.

In some embodiments disclosed herein the PCR master mix encompasses a biological buffer, a mesylate, and a polymerase. In some embodiments the biological buffer is Tris-mesylate. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the PCR master mix encompasses a mesylate, wherein the mesylate is potassium methanesulfonate. In some embodiments, the potassium methanesulfonate is present from 30-80 mM. In other embodiments, the potassium methanesulfonate is present at about 35 mM, 40 mM, 45 mM, 50 mM, 55 mM, 60 mM, 65 mM, 70 mM, or 75 mM. In other embodiments, the mesylate is magnesium methanosulfate. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM. In some embodiments, the polymerase is a DNA polymerase.

In some embodiments, the PCR master mix encompasses Tris-mesylate (30 mM; pH 8.3), potassium methanesulfate (35 mM), and a DNA polymerase.

In some embodiments, the PCR master mix encompasses a mesylate, a proteinaceous compound and a polymerase. In some embodiments the biological buffer is Tris-mesylate and the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the PCR master mix encompasses a mesylate, a proteinaceous compound and magnesium sulfate wherein the mesylate is potassium methanesulfonate. In some embodiments, the potassium methanesulfonate is present from 30-80 mM. In other embodiments, the potassium methanesulfonate is present at about 35 mM, 40 mM, 45 mM, 50 mM, 55 mM, 60 mM, 65 mM, 70 mM, or 75 mM. In some embodiments, the mesylate is magnesium methanosulfate. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM. In some embodiments, the PCR master mix encompasses a mesylate, a proteinaceous compound and magnesium sulfate, wherein the proteinaceous compound is albumin. In some embodiments the albumin is present in the PCR master mix at 1.2-4 mg/ml. In some embodiments the albumin is present in the PCR master mix at 1.5, 2, 2.5, 3, or 3.5 mg/ml. In some instances the albumin is bovine serum albumin. In some embodiments the bovine serum albumin is present in the PCR master mix at 1.2-4 mg/ml. In some embodiments the bovine serum albumin is present in the PCR master mix at 1.5, 2, 2.5, 3, or 3.5 mg/ml. In some embodiments the proteinaceous compound is gelatin. In some embodiments, the PCR master mix encompasses a mesylate, a proteinaceous compound and a DNA polymerase.

In some embodiments, the PCR master mix encompasses Tris-mesylate (30 mM; pH 8.3), potassium methanesulfate (35 mM), bovine serum albumin (2 mg/ml) and a DNA polymerase.

In some embodiments, the PCR master mix encompasses a mesylate, a stabilizer compound and a polymerase. In some embodiments, the PCR master mix encompasses Tris-mesylate, a mesylate, a stabilizer compound and a polymerase. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the PCR master mix encompasses a mesylate, a stabilizer compound and a polymerase wherein the mesylate is potassium methanesulfonate. In some embodiments, the potassium methanesulfonate is present from 30-80 mM. In other embodiments, the potassium methanesulfonate is present at about 35 mM, 40 mM, 45 mM, 50 mM, 55 mM, 60 mM, 65 mM, 70 mM, or 75 mM. In some embodiments, the mesylate is magnesium methanosulfate. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM. In some embodiments, the PCR master mix encompasses a mesylate, a stabilizer compound and a polymerase, wherein the stabilizer compound is glycerol. In some embodiments the glycerol is present in the PCR master mix at 3-8%. In some embodiments the glycerol is present in the PCR master mix at 3.5, 4, 4.5, 5, 5.5, 6, 6.5, 7, or 7.5%. In other embodiments, the stabilizer compound is sucrose. In some embodiments, the PCR master mix encompasses a mesylate, a stabilizer compound and a polymerase, wherein the polymerase is a DNA polymerase.

In some embodiments, the PCR master mix encompasses Tris-mesylate (30 mM; pH 8.3), potassium methanesulfate (35 mM), glycerol (5%) and a DNA polymerase.

In some embodiments, the PCR master mix encompasses a mesylate, a non-ionic detergent, and a polymerase. In some embodiments, the PCR master mix encompasses Tris-mesylate, a mesylate, and a polymerase. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the PCR master mix encompasses a mesylate, a proteinaceous compound and a stabilizer compound wherein the mesylate is potassium methanesulfonate. In some embodiments, the potassium methanesulfonate is present from 30-80 mM. In other embodiments, the potassium methanesulfonate is present at about 35 mM, 40 mM, 45 mM, 50 mM, 55 mM, 60 mM, 65 mM, 70 mM, or 75 mM. In some embodiments, the mesylate is magnesium methanosulfate. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM. In some embodiments, the PCR master mix encompasses a mesylate, a non-ionic detergent and a polymerase, wherein the non-ionic detergent is present from 0.1-0.9%. In some embodiments the non-ionic detergent is polysorbate 20. In some embodiments, the polysorbate 20 is present from 0.1-0.9%. In some embodiments, the polysorbate 20 is present at 0.2%. In some embodiments, the PCR master mix encompasses a mesylate, a non-ionic detergent and a polymerase, wherein the polymerase is a DNA polymerase.

In some embodiments, the PCR master mix encompasses Tris-mesylate (30 mM, pH 8.3), potassium methanesulfonate (35 mM), polysorbate 20 (0.2%) and a DNA polymerase.

In some embodiments, the PCR master mix encompasses a mesylate, a proteinaceous compound, a stabilizer compound, a non-ionic detergent, magnesium sulfate and a polymerase. In some embodiments, the PCR master mix encompasses Tris-mesylate, a mesylate, a proteinaceous compound, a stabilizer compound, a non-ionic detergent and magnesium sulfate. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the PCR master mix encompasses a mesylate, a proteinaceous compound, a stabilizer compound, a non-ionic detergent and magnesium sulfate wherein the mesylate is potassium methanesulfonate. In some embodiments, the potassium methanesulfonate is present from 30-80 mM. In other embodiments, the potassium methanesulfonate is present at about 35 mM, 40 mM, 45 mM, 50 mM, 55 mM, 60 mM, 65 mM, 70 mM, or 75 mM. In some embodiments, the mesylate is magnesium methanosulfate. In some embodiments, the magnesium methanosulfonate is present at 1.2-

1.8 mM. In other embodiments, the magnesium methanosulfonate is present at about 1.3 mM, 1.4 mM, 1.5 mM, 1.6 mM, or 1.7 mM. In some embodiments, the PCR master mix encompasses a mesylate, a proteinaceous compound, a stabilizer compound, a non-ionic detergent and magnesium sulfate, wherein the proteinaceous compound is albumin. In some embodiments the albumin is present in the PCR master mix at 1.2-4 mg/ml. In some embodiments the albumin is present in the PCR master mix at 1.5, 2, 2.5, 3, or 3.5 mg/ml. In some embodiments the albumin is bovine serum albumin. In some embodiments the bovine serum albumin is present in the PCR master mix at 1.2-4 mg/ml. In some embodiments the bovine serum albumin is present in the PCR master mix at 1.5, 2, 2.5, 3, or 3.5 mg/ml. In some embodiments the proteinaceous compound is gelatin. In some embodiments, the PCR master mix encompasses a mesylate, a proteinaceous compound, a stabilizer compound, a non-ionic detergent and magnesium sulfate wherein the stabilizer compound is glycerol. In some embodiments the glycerol is present in the PCR master mix at 1.2-8%. In some embodiments the glycerol is present in the PCR master mix at 2, 3.0 3.5, 4, 4.5, 5, 5.5, 6, 6.5, 7, or 7.5%. In other embodiments, the stabilizer compound is sucrose. In some embodiments, the PCR master mix encompasses a mesylate, a proteinaceous compound, a stabilizer compound, a non-ionic detergent and magnesium sulfate, wherein the non-ionic detergent is present from 0.1-0.9%. In some embodiments the non-ionic detergent is polysorbate 20. In some embodiments, the polysorbate 20 is present from 0.1-0.9%. In some embodiments, the polysorbate 20 is present at 0.2%. In some embodiments, the PCR master mix encompasses a mesylate, a proteinaceous compound, a stabilizer compound, a non-ionic detergent and magnesium sulfate, wherein the magnesium sulfate is at 1.2-2.4 mM. In some embodiments the magnesium sulfate is at 1.6 mM. In some embodiments, the polymerase is a DNA polymerase.

In some embodiments, the PCR master mix encompasses Tris-mesylate (30 mM, pH 8.3), potassium methanesulfonate (35 mM), bovine serum albumin (2 mg/ml), glycerol (5%), polysorbate 20 (0.2%), magnesium sulfate (1.6 mM) and a DNA polymerase.

In some embodiments, the PCR master mix encompasses nucleoside triphosphates. In some embodiments the nucleoside triphosphates are deoxynucleoside triphosphates, such as deoxyadenosine triphosphate, deoxycytidine triphosphate, deoxyguanosine triphosphate and deoxythymidine triphosphate; collectively "dNTPs".

In some embodiments disclosed herein the PCR master mix encompasses a biological buffer, a mesylate, and nucleoside triphosphates. In some embodiments the biological buffer is Tris-mesylate. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the PCR master mix encompasses a mesylate, wherein the mesylate is potassium methanesulfonate. In some embodiments, the potassium methanesulfonate is present from 30-80 mM. In other embodiments, the potassium methanesulfonate is present at about 35 mM, 40 mM, 45 mM, 50 mM, 55 mM, 60 mM, 65 mM, 70 mM, or 75 mM. In other embodiments, the mesylate is magnesium methanosulfate. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM. In some embodiments, each nucleoside triphosphate is 150-250 µM. In some embodiments, each nucleoside triphosphate is 200 µM. In some embodiments, the nucleoside triphosphates are dNTPs. In some embodiments, each deoxynucleoside triphosphate is 150-250 µM. In some embodiments, each deoxynucleoside triphosphate is 200 µM.

In some embodiments, the PCR master mix encompasses Tris-mesylate (30 mM; pH 8.3), potassium methanesulfate (35 mM), and dNTPs (each deoxynucleoside triphosphate 200 µM).

In some embodiments, the PCR master mix encompasses a mesylate, a proteinaceous compound and nucleoside triphosphates. In some embodiments the biological buffer is Tris-mesylate and the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the PCR master mix encompasses a mesylate, a proteinaceous compound and magnesium sulfate wherein the mesylate is potassium methanesulfonate. In some embodiments, the potassium methanesulfonate is present from 30-80 mM. In other embodiments, the potassium methanesulfonate is present at about 35 mM, 40 mM, 45 mM, 50 mM, 55 mM, 60 mM, 65 mM, 70 mM, or 75 mM. In some embodiments, the mesylate is magnesium methanosulfate. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM. In some embodiments, the PCR master mix encompasses a mesylate, a proteinaceous compound and magnesium sulfate, wherein the proteinaceous compound is albumin. In some embodiments the albumin is present in the PCR master mix at 1.2-4 mg/ml. In some embodiments the albumin is present in the PCR master mix at 1.5, 2, 2.5, 3, or 3.5 mg/ml. In some instances the albumin is bovine serum albumin. In some embodiments the bovine serum albumin is present in the PCR master mix at 1.2-4 mg/ml. In some embodiments the bovine serum albumin is present in the PCR master mix at 1.5, 2, 2.5, 3, or 3.5 mg/ml. In some embodiments the proteinaceous compound is gelatin. In some embodiments, the PCR master mix encompasses a mesylate, a proteinaceous compound and nucleoside triphosphate. In some embodiments, each nucleoside triphosphate is 150-250 µM. In some embodiments, each nucleoside triphosphate is 200 µM. In some embodiments, the nucleoside triphosphates are dNTPs. In some embodiments, each deoxynucleoside triphosphate is 150-250 µM. In some embodiments, each deoxynucleoside triphosphate is 200 µM.

In some embodiments, the PCR master mix encompasses Tris-mesylate (30 mM; pH 8.3), potassium methanesulfate (35 mM), bovine serum albumin (2 mg/ml) and dNTPs (each deoxynucleoside triphosphate 200 µM).

In some embodiments, the PCR master mix encompasses a mesylate, a stabilizer compound and a nucleoside triphosphate. In some embodiments, the PCR master mix encompasses Tris-mesylate, a mesylate, a stabilizer compound and a nucleoside triphosphate. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the PCR master mix encompasses a mesylate, a stabilizer compound and a nucleoside triphosphate wherein the mesylate is potassium methanesulfonate. In some embodiments, the potassium methanesulfonate is present from 30-80 mM. In other embodiments, the potassium methanesulfonate is present at about 35 mM, 40 mM, 45 mM, 50 mM, 55 mM, 60 mM, 65 mM, 70 mM, or 75 mM. In some embodiments, the mesylate is magnesium methanosulfate. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM. In some embodiments, the PCR master mix encompasses a mesylate, a stabilizer compound and a polymerase, wherein the stabilizer compound is glycerol. In some embodiments the glycerol is present in the PCR master mix at 3-8%. In some embodiments the glycerol is present in the PCR master mix at 3.5, 4, 4.5, 5, 5.5, 6, 6.5, 7, or 7.5%. In other embodiments, the stabilizer compound is sucrose. In some embodiments, the PCR master mix encompasses a mesylate, a stabilizer compound and a nucleoside triphosphate. In some embodiments, each nucleoside triphosphate is 150-250 µM. In some embodiments, each nucleoside triphosphate is 200 µM. In some embodiments, the nucleoside triphosphates are dNTPs. In some embodiments, each deoxynucleoside triphosphate is 150-250 µM. In some embodiments, each deoxynucleoside triphosphate is 200 µM.

In some embodiments, the PCR master mix encompasses Tris-mesylate (30 mM; pH 8.3), potassium methanesulfate (35 mM), glycerol (5%) and a dNTPs (each deoxynucleoside triphosphate 200 µM).

In some embodiments, the PCR master mix encompasses a mesylate, a non-ionic detergent, and a nucleoside triphosphate. In some embodiments, the PCR master mix encompasses Tris-mesylate, a mesylate, and a nucleoside triphosphate. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the PCR master mix encompasses a mesylate, a non-ionic detergent and a nucleoside triphosphate wherein the mesylate is potassium methanesulfonate. In some embodiments, the potassium methanesulfonate is present from 30-80 mM. In other embodiments, the potassium methanesulfonate is present at about 35 mM, 40 mM, 45 mM, 50 mM, 55 mM, 60 mM, 65 mM, 70 mM, or 75 mM. In some embodiments, the mesylate is magnesium methanosulfate. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM. In some embodiments, the PCR master mix encompasses a mesylate, a non-ionic detergent and a nucleoside triphospahte, wherein the non-ionic detergent is present from 0.1-0.9%. In some embodiments the non-ionic detergent is polysorbate 20. In some embodiments, the polysorbate 20 is present at 0.2%. In some embodiments, the PCR master mix encompasses a mesylate, a non-ionic detergent and a nucleoside triphosphate. In some embodiments, each nucleoside triphosphate is 150-250 µM. In some embodiments, each nucleoside triphosphate is 200 µM. In some embodiments, the nucleoside triphosphates are dNTPs. In some embodiments, each deoxynucleoside triphosphate is 150-250 µM. In some embodiments, each deoxynucleoside triphosphate is 200 µM.

In some embodiments, the PCR master mix encompasses Tris-mesylate (30 mM, pH 8.3), potassium methanesulfonate (35 mM), polysorbate 20 (0.2%) and a dNTPs (each deoxynucleoside triphosphate 200 µM).

In some embodiments, the PCR master mix encompasses a mesylate, a proteinaceous compound, a stabilizer compound, a non-ionic detergent, magnesium sulfate, a polymerase and a deoxynucleoside triphosphate. In some embodiments, the PCR master mix encompasses Tris-mesylate, a mesylate, a proteinaceous compound, a stabilizer compound, a non-ionic detergent and magnesium sulfate. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In some embodiments, the PCR master mix encompasses a mesylate, a proteinaceous compound, a stabilizer compound, a non-ionic detergent and magnesium sulfate wherein the mesylate is potassium methanesulfonate. In some embodiments, the potassium methanesulfonate is present from 30-80 mM. In other embodiments, the potassium methanesulfonate is present at about 35 mM, 40 mM, 45 mM, 50 mM, 55 mM, 60 mM, 65 mM, 70 mM, or 75 mM. In some embodiments, the mesylate is magnesium methanosulfate. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM. In some embodiments, the PCR master mix encompasses a mesylate, a proteinaceous compound, a stabilizer compound, a non-ionic detergent and magnesium sulfate, wherein the proteinaceous compound is albumin. In some embodiments the albumin is present in the PCR master mix at 1.2-4 mg/ml. In some embodiments the albumin is present in the PCR master mix at 1.5, 2, 2.5, 3, or 3.5 mg/ml. In some instances the albumin is bovine serum albumin. In some embodiments the bovine serum albumin is present in the PCR master mix at 1.2-4 mg/ml. In some embodiments the bovine serum albumin is present in the PCR master mix at 1.5, 2, 2.5, 3, or 3.5 mg/ml. In some embodiments the proteinaceous compound is gelatin. In some embodiments, the PCR master mix encompasses a mesylate, a proteinaceous compound, a stabilizer compound, a non-ionic detergent and magnesium sulfate wherein the stabilizer compound is glycerol. In some embodiments the glycerol is present in the PCR master mix at 3-8%. In some embodiments the glycerol is present in the PCR master mix at 3.5, 4, 4.5, 5, 5.5, 6, 6.5, 7, or 7.5%. In other embodiments, the stabilizer compound is sucrose. In some embodiments, the PCR master mix encompasses a mesylate, a proteinaceous compound, a stabilizer compound, a non-ionic detergent and magnesium sulfate, wherein the non-ionic detergent is present from 0.1-0.9%. In some embodiments the non-ionic detergent is polysorbate 20. In some embodiments, the polysorbate 20 is present from 0.1-0.9%. In some embodiments, the polysorbate 20 is present at 0.2%. In some embodiments, the PCR master mix encompasses a mesylate, a proteinaceous compound, a stabilizer compound, a non-ionic detergent and magnesium sulfate, wherein the magnesium sulfate is at 1.2-2.4 mM. In some embodiments the magnesium sulfate is at 1.6 mM. In some embodiments, the polymerase is a DNA polymerase. In some embodiments, each nucleoside triphosphate is 150-250 µM. In some embodiments, each nucleoside triphosphate is 200 µM. In some embodiments, the nucleoside triphosphates are dNTPs. In some embodiments, each deoxynucleoside triphosphate is 150-250 µM. In some embodiments, each deoxynucleoside triphosphate is 200 µM.

In some embodiments, the PCR master mix encompasses Tris-mesylate (30 mM, pH 8.3), potassium methanesulfonate (35 mM), bovine serum albumin (2 mg/ml), glycerol (5%), polysorbate 20 (0.2%), magnesium sulfate (1.6 mM), a DNA polymerase and a dNTPs (each deoxynucleoside triphosphate 200 µM).

A tabular view of non-limiting embodiments of the PCR master mix is shown in Table 1. Values represent the final working concentration of the reagent.

TABLE 1

| Reagent | Range | | Unit |
|---|---|---|---|
| UnitTris (pH 8.3) | 10 | 50 | mM |
| Potassium methanesulfate | 30 | 80 | mM |
| Magnesium sulfate | 1.2 | 2.4 | mM |
| Glycerol | 3 | 8 | % |
| dNTP | 0.15 | 0.25 | mM |
| Polysorbate 20 | 0.1 | 0.9 | % |
| Bovine serum albumin | 1.2 | 4 | Mg/ml |

In some embodiments, the PCR master mix encompasses sodium azide. In some embodiments the sodium azide is 0.01-0.04%. In some embodiments, the sodium azide is 0.02%.

Thus, in some embodiments, the PCR master mix encompasses Tris-mesylate (30 mM, pH 8.3), potassium methanesulfonate (35 mM), bovine serum albumin (2 mg/ml), glycerol (5%), polysorbate 20 (0.2%), magnesium sulfate (1.6 mM), a DNA polymerase, dNTPs (each deoxynucleoside triphosphate 200 µM) and sodium azide (0.02%).

Kits

Disclosed herein are kits. "Kit" refers to a set of articles or implements which can be used in conjunction with one another to achieve a specific purpose.

In some embodiments a kit is disclosed, the kit encompassing a first capped tube, or other form of fluid conveyance, containing a PCR master mix encompassing a mesylate as disclosed herein. In some embodiments the mesylate is potassium methanesulfonate. In some embodiments, the potassium methanesulfonate is present from 30-80 mM. In other embodiments, the potassium methanesulfonate is present at about 35 mM, 40 mM, 45 mM, 50 mM, 55 mM, 60 mM, 65 mM, 70 mM, or 75 mM. In some embodiments, the mesylate is magnesium methanosulfate. In some embodiments, the magnesium methanosulfonate is present at 1.2-1.8 mM. In other embodiments, the magnesium methanosulfonate is present at about 1.3 mM, 1.4 mM, 1.5 mM, 1.6 mM, or 1.7 mM. In some embodiments the PCR master mix disclosed herein encompasses Tris-mesylate and a mesylate. In some embodiments the Tris-mesylate is present in the PCR master mix at 10-50 mM. In other embodiments, the Tris-mesylate is present in the PCR master mix at about 10 mM, 15 mM, 20 mM, 25 mM, 30 mM, 35 mM, 40 mM, or 45 mM. In some embodiments, the Tris-mesylate has a pH of about 7.0. In some embodiments, the Tris-mesylate has a pH of about 8.0. In other embodiments, the Tris-mesylate has a pH of about 9.0. In other embodiments, the PCR master mix encompasses a mesylate and a proteinaceous compound. In some embodiments the proteinaceous compound is albumin. In some embodiments the albumin is present in the PCR master mix at 1.2-4 mg/ml. In some embodiments the albumin is present in the PCR master mix at 1.5, 2, 2.5, 3, or 3.5 mg/ml. In some instances the albumin is bovine serum albumin. In some embodiments the bovine serum albumin is present in the PCR master mix at 1.2-4 mg/ml. In some embodiments the bovine serum albumin is present in the PCR master mix at 1.5, 2, 2.5, 3, or 3.5 mg/ml. In some embodiments, the PCR master mix encompasses Tris-mesylate, a mesylate and a proteinaceous compound. In some embodiments, the PCR master mix encompasses a mesylate and a stabilizer compound. In some embodiments the stabilizer compound is glycerol. In some embodiments the glycerol is present in the PCR master mix at 3-8%. In some embodiments the glycerol is present in the PCR master mix at 3.5, 4, 4.5, 5, 5.5, 6, 6.5, 7, or 7.5%. In some embodiments, the PCR master mix encompasses Tris-mesylate, a mesylate and a stabilizer compound. In some embodiments, the PCR master mix encompasses a mesylate, a stabilizer compound and a proteinaceous compound. In some embodiments, the PCR master mix encompasses Tris-mesylate, a mesylate, a stabilizer compound and a proteinaceous compound.

In some embodiments, the PCR master mix encompasses a mesylate and a polymerase. In some embodiments, the PCR master mix encompasses Tris-mesylate, a mesylate and a polymerase. In some embodiments, the PCR master mix encompasses a mesylate, a stabilizer compound and a polymerase. In some embodiments, the PCR master mix encompasses Tris-mesylate, a mesylate, a stabilizer compound and a polymerase. In some embodiments, the PCR master mix encompasses a mesylate, a proteinaceous compound and a polymerase. In some embodiments, the PCR master mix encompasses Tris-mesylate, a mesylate, a proteinaceous compound and a polymerase. In some embodiments, the PCR master mix encompasses a mesylate, a stabilizer compound, a proteinaceous compound and a polymerase. In some embodiments, the PCR master mix encompasses Tris-mesylate, a mesylate, a stabilizer compound, a proteinaceous compound and a polymerase.

In some embodiments a kit is disclosed, the kit encompassing a first capped tube, or other form of fluid conveyance, containing a PCR master mix encompassing a mesylate and a second capped tube, or other form of fluid conveyance, containing a polymerase.

In other embodiments a kit is disclosed, the kit encompassing a first capped tube, or other form of fluid conveyance, containing a PCR master mix encompassing a mesylate, as disclosed herein, and a second capped tube, or other form of fluid conveyance, containing a primer. A "primer" refers to an oligonucleotide, which is a reverse complement to a template polynucleotide sequence and is capable of acting as a point for the initiation of polymerase mediated nucleotide extension. In some embodiments, the primer is present at 100-350 µM.

A "primer pair" refers to two primers that are the reverse complement of opposite strands of a double stranded polynucleotide. In other embodiments a kit is disclosed, the kit encompassing a first capped tube, or other form of fluid conveyance, containing a PCR master mix encompassing a mesylate, as disclosed herein, and a second capped tube, or other form of fluid conveyance, containing a primer pair. In some embodiments, each primer of the primer pair is present at 100-350 µM. In some embodiments, the primer pair flanks a short tandem repeat locus.

In some embodiments, the second capped tube, or other form of fluid conveyance, contains 1-1000 primer pairs, from 1-500 primer pairs, from 1-200 primer pairs, from 1-100 primer pairs, from 1-99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2 primer pairs. In other embodiments, the second capped tube, or other form of fluid conveyance, contains 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3 or 2 primer pairs.

In some embodiments a kit is disclosed, the kit encompassing a first capped tube, or other form of fluid conveyance, containing a PCR master mix encompassing a mesylate, as disclosed herein, and a second capped tube, or other form of fluid conveyance, containing an allelic ladder.

"Allelic ladder" refers to a nucleic acid size standard that provides size standards for one or more alleles for a particular short tandem repeat ("STR") marker. The allelic ladder serves as a reference standard and nucleic acid size marker for the amplified alleles from the STR locus. In some embodiments, the allelic ladder can comprise size standards for the alleles of different STRs. In some embodiments, the allelic ladder can be made of DNA. In some embodiments the allelic ladder can be made of non-naturally occurring nucleic acid analogs. The different individual size standards within an allelic ladder can, in some embodiments can be labeled with a detectable label, e.g., a fluorophore. In some embodiments, the allelic ladder components are labeled with the same fluorophore. In some embodiments, the allelic ladder components are labeled with the different fluorophores. The size standards can be selected to work for a specific pair (or pairs) of oligonucleotides primers. For example if a first set of primers for marker X produces a 150 base pair amplicon corresponding to allele 7, the corresponding marker will serve as a size standard for the 150 base amplicons; while a second pair of primers marker X produces a 175 base pair amplicon corresponding to allele 7, the corresponding marker will serve as a size standard for the 175 base amplicons. Thus different size standards for different size amplicons of the same allele are contemplated. The size standard for a given amplicon derived from a given allele may have nucleic acid base sequence that is the same or different than the nucleic acid base sequence of the amplicon or allele from which the amplicon is derived. For allele analysis in electrophoresis systems the size standard can be selected so as to have the same electrophoretic mobility as the amplicon of interest. Alternatively, in some embodiments, the size standard can be selected so as to have the different electrophoretic mobility than the amplicon of interest, given an understanding of the predicable nature of the difference, the identity of the amplicons could be determined. For allele analysis in mass spectroscopy systems the size standard (weight/charge ratio, not electrophoretic mobility) can be selected so as to have the same signal as the amplicon of interest. Alternatively, in some embodiments, the size standard (weight/charge ratio, not electrophoretic mobility) can be selected so as to have the different separation properties than the amplicon of interest, given an understanding of the predicable nature of the difference, the identity of the amplicons could be determined.

In other embodiments a kit is disclosed, the kit encompassing a first capped tube, or other form of fluid conveyance, containing a PCR master mix encompassing a mesylate, as disclosed herein, and a second capped tube, or other form of fluid conveyance, containing a primer and a third capped tube, or other form of fluid conveyance, containing an allelic ladder.

Method

In some embodiments a method is disclosed. The disclosed method entails contacting a sample with a composition encompassing a mesylate, and subjecting this combination to PCR amplification.

A "sample" refers to a solid or liquid suspected of containing a nucleic acid. The sample can be, for instance, blood, saliva, buccal, semen or vaginal fluids. The sample can be a filter paper upon which cells have been collected; for instance, buccal cells, blood cells, semen or vaginal fluids. The sample can be a filter paper having been contacted to a surface, for instance a surface on which there is a fingerprint. The sample can be a swab, or a portion thereof, upon which cells have collected; for instance, buccal cells, blood cells, semen or vaginal fluids. The swab can be made of materials such as cotton or Nylon®. The sample can be a swab having been contacted to a surface; for instance a surface on which there is a fingerprint, blood, saliva or vaginal fluids.

In some embodiments, the method encompasses contacting a sample with a composition wherein the composition encompasses potassium methanesulfonate (30-80 mM). In other embodiments of the method, the composition encompasses magnesium methanosulfonate (1.2-1.8 mM). In some embodiments of the method, the composition encompasses Tris-mesylate (10-50 mM) and potassium methanesulfonate (30-80 mM). In some embodiments of the method, the composition encompasses Tris-mesylate (10-50 mM) and magnesium methanosulfonate (1.2-1.8 mM). In some embodiments of the method, the composition encompasses a mesylate and a proteinaceous compound. In some embodiments of the method, the proteinaceous compound is albumin. In some embodiments of the method, the albumin is bovine serum albumin (1.2-6.0 mg/ml). In some embodiments of the method, the composition encompasses Tris-mesylate-HCl (10-50 mM), potassium methanesulfonate (30-80 mM) and bovine serum albumin (1.2-6.0 mg/ml). In some embodiments of the method, the composition encompasses a mesylate and a stabilizer compound. In some embodiments of the method, the stabilizer compound is glycerol. In some embodiments of the method, the glycerol is present in the composition at 1.2-8%. In some embodiments of the method the glycerol is present in the composition at 2, 3.0 3.5, 4, 4.5, 5, 5.5, 6, 6.5, 7, or 7.5%. In other embodiments of the method, the stabilizer compound is sucrose. In some embodiments of the method, the composition encompasses a mesylate, a proteinaceous compound, a stabilizer compound, a non-ionic detergent and magnesium sulfate, wherein the non-ionic detergent is present from 0.1-0.9%. In some embodiments of the method the non-ionic detergent is polysorbate 20. In some embodiments of the method, the polysorbate 20 is present from 0.1-0.9%. In some embodiments of the method, the polysorbate 20 is present at 0.2%. In some embodiments of the method, the composition encompasses a mesylate, a proteinaceous compound, a stabilizer compound, a non-ionic detergent and magnesium sulfate, wherein the magnesium sulfate is at 1.2-2.4 mM. In some embodiments of the method the magnesium sulfate is at 1.6 mM. In some embodiments of the method, the composition encompasses a mesylate and a polymerase. In some embodiments of the method, the polymerase is a DNA polymerase. In some embodiments of the method, the DNA polymerase is Taq.

In some embodiments of the method, the composition encompasses Tris-mesylate (10-50 mM), potassium methanesulfonate (30-80 mM), bovine serum albumin (1.2-4 mg/ml), glycerol (3-8% volume), MgSO$_4$ (1.4-2.4 mM), Sodium Azide (0.01-0.04%), dATP (150-250 mM), dCTP (150-250 mM), dGTP (150-250 mM), dTTP (150-250 mM), a primer pair and a DNA polymerase.

In some embodiments the method disclosed entails contacting a sample with a composition wherein the sample encompasses a nucleic acid and the composition encompasses Tris-mesylate-HCl (10-50 mM), potassium methanesulfonate (30-80 mM), bovine serum albumin (1.2-4 mg/ml), glycerol (3-8% volume), MgSO$_4$ (1.4-2.4 mM), Sodium Azide (0.01-0.04%), dATP (150-250 mM), dCTP (150-250 mM), dGTP (150-250 mM), dTTP (150-250 mM), a primer pair and a DNA polymerase. In some embodiments the method disclosed entails contacting a sample with a composition wherein the sample encompasses buccal cells and the composition encompasses Tris-mesylate-HCl (10-50 mM), potassium methanesulfonate (30-80 mM), bovine serum albumin (1.2-4 mg/ml), glycerol (3-8% volume), MgSO$_4$ (1.4-2.4 mM), Sodium Azide (0.01-0.04%), dATP (150-250 mM), dCTP (150-250 mM), dGTP (150-250 mM), dTTP (150-250 mM), a primer pair and a DNA polymerase. In some embodiments the method disclosed entails contacting a sample with a composition wherein the sample encompasses blood cells and the composition encompasses Tris-mesylate-HCl (10-50 mM), potassium methanesulfonate (30-80 mM), bovine serum albumin (1.2-4 mg/ml), glycerol (3-8% volume), MgSO$_4$ (1.4-2.4 mM), Sodium Azide (0.01-0.04%), dATP (150-250 mM), dCTP (150-250 mM), dGTP (150-250 mM), dTTP (150-250 mM), a primer pair and a DNA polymerase. In some embodiments the method disclosed entails contacting a sample with a composition wherein the sample encompasses filter paper and the composition encompasses Tris-mesylate-HCl (10-50 mM), potassium methanesulfonate (30-80 mM), bovine serum albumin (1.2-4 mg/ml), glycerol (3-8% volume), MgSO$_4$ (1.4-2.4 mM), Sodium Azide (0.01-0.04%), dATP (150-250 mM), dCTP (150-250 mM), dGTP (150-250 mM), dTTP (150-250 mM), a primer pair and a DNA polymerase. In some embodiments the method disclosed entails contacting a sample with a composition wherein the sample encompasses filter paper suspected of possessing a nucleic acid and the composition encompasses Tris-mesylate-HCl (10-50 mM), potassium methanesulfonate (30-80 mM), bovine serum albumin (1.2-4 mg/ml), glycerol (3-8% volume), MgSO$_4$ (1.4-2.4 mM), Sodium Azide (0.01-0.04%), dATP (150-250 mM), dCTP (150-250 mM), dGTP (150-250 mM), dTTP (150-250 mM), a primer pair and a DNA polymerase. In some embodiments the method disclosed entails contacting a sample with a composition wherein the sample encompasses filter paper encompassing buccal or blood cells and the composition encompasses Tris-mesylate-HCl (10-50 mM), potassium methanesulfonate (30-80 mM), bovine serum albumin (1.2-4 mg/ml), glycerol (3-8% volume), MgSO$_4$ (1.4-2.4 mM), Sodium Azide (0.01-0.04%), dATP (150-250 mM), dCTP (150-250 mM), dGTP (150-250 mM), dTTP (150-250 mM), a primer pair and a DNA polymerase.

In some embodiments the method disclosed entails contacting a sample with a composition encompassing a mesylate and thereby forming a contacted sample, and subjecting the contacted sample to a thermocycling protocol and thereby forming a cycled sample. A "thermocycling protocol" refers to bringing a contacted sample to a first temperature and a second temperature, or a first, a second and a third temperature, with repetition of the temperature routine. Non-limiting examples of a thermocycling protocol are bringing a contacted sample to a temperature of 95° C. and then to 65° C. and then back to 95° C. or 95° C. then to 55° C. and then to 72° C. and then back to 95° C. Each of these temperatures are maintained for various amounts of time; routinely from a second to several minutes.

Thus, in some embodiments of the method, the contacted sample is brought to a first temperature, then to a second temperature and then back to the first temperature at least 15 times, but not more than 50 times. In some embodiments of the method, the contacted sample is brought to a first temperature, then to a second temperature and then back to the first temperature at least 20 times, but not more than 50 times. In some embodiments of the method, the contacted sample is brought to a first temperature, then to a second temperature and then back to the first temperature at least 25 times, but not more than 50 times. In some embodiments of the method, the contacted sample is brought to a first temperature, then to a second temperature and then back to the first temperature at least 25 times, but not more than 35 times.

In some embodiments of the method, the contacted sample is brought to a first temperature, then to a second temperature, then to a third and then back to the first temperature at least 15 times, but not more than 50 times. In some embodiments of the method, the contacted sample is brought to a first temperature, then to a second temperature, then to a third and then back to the first temperature at least 20 times, but not more than 50 times. In some embodiments of the method, the contacted sample is brought to a first temperature, then to a second temperature, then to a third temperature and then back to the first temperature at least 25 times, but not more than 50 times. In some embodiments of the method, the contacted sample is brought to a first temperature, then to a second temperature, then to a third temperature and then back to the first temperature at least 25 times, but not more than 35 times.

In some embodiments a method is disclosed entailing contacting a sample with a composition and thereby forming a contacted sample and subjecting the contacted sample to a thermocycling protocol and thereby forming a cycled sample wherein the sample encompasses a nucleic acid, the composition encompasses Tris-mesylate (10-50 mM), potassium methanesulfonate (30-80 mM), bovine serum albumin (1.2-4 mg/ml), glycerol (3-8% volume), MgSO$_4$ (1.4-2.4 mM), Sodium Azide (0.01-0.04%), dATP (150-250 mM), dCTP (150-250 mM), dGTP (150-250 mM), dTTP (150-250 mM), a primer pair and a DNA polymerase and the thermocycling protocol encompasses bringing the contacted sample to a first temperature, then to a second temperature and then back to the first temperature at least 15 times, but not more than 50 times. In other embodiments, the thermocycling protocol encompasses bringing the contacted sample to a first temperature, then to a second temperature, then to a third and then back to the first temperature at least 15 times, but not more than 50 times.

In some embodiments the method disclosed entails contacting a sample with a composition and thereby forming a contacted sample and subjecting the contacted sample to a thermocycling protocol and thereby forming a cycled sample wherein the sample encompasses buccal cells, the composition encompasses Tris-mesylate (10-50 mM), potassium methanesulfonate (30-80 mM), bovine serum albumin (1.2-4 mg/ml), glycerol (3-8% volume), $MgSO_4$ (1.4-2.4 mM), Sodium Azide (0.01-0.04%), dATP (150-250 mM), dCTP (150-250 mM), dGTP (150-250 mM), dTTP (150-250 mM), a primer pair and a DNA polymerase and the thermocycling protocol encompasses bringing the contacted sample to a first temperature, then to a second temperature and then back to the first temperature at least 15 times, but not more than 50 times. In other embodiments, the thermocycling protocol encompasses bringing the contacted sample to a first temperature, then to a second temperature, then to a third and then back to the first temperature at least 15 times, but not more than 50 times.

In some embodiments the method disclosed entails contacting a sample with a composition and thereby forming a contacted sample and subjecting the contacted sample to a thermocycling protocol and thereby forming a cycled sample wherein the sample encompasses blood cells, the composition encompasses Tris-mesylate (10-50 mM), potassium methanesulfonate (30-80 mM), bovine serum albumin (1.2-4 mg/ml), glycerol (3-8% volume), $MgSO_4$ (1.4-2.4 mM), Sodium Azide (0.01-0.04%), dATP (150-250 mM), dCTP (150-250 mM), dGTP (150-250 mM), dTTP (150-250 mM), a primer pair and a DNA polymerase and the thermocycling protocol encompasses bringing the contacted sample to a first temperature, then to a second temperature and then back to the first temperature at least 15 times, but not more than 50 times. In other embodiments, the thermocycling protocol encompasses bringing the contacted sample to a first temperature, then to a second temperature, then to a third and then back to the first temperature at least 15 times, but not more than 50 times.

In some embodiments the method disclosed entails contacting a sample with a composition and thereby forming a contacted sample, subjecting the contacted sample to a thermocycling protocol and thereby forming a cycled sample wherein the sample encompasses filter paper suspected of possessing a nucleic acid, the composition encompasses Tris-mesylate (10-50 mM), potassium methanesulfonate (30-80 mM), bovine serum albumin (1.2-4 mg/ml), glycerol (3-8% volume), $MgSO_4$ (1.4-2.4 mM), Sodium Azide (0.01-0.04%), dATP (150-250 mM), dCTP (150-250 mM), dGTP (150-250 mM), dTTP (150-250 mM), a primer pair and a DNA polymerase and the thermocycling protocol encompasses bringing the contacted sample to a first temperature, then to a second temperature and then back to the first temperature at least 15 times, but not more than 50 times. In other embodiments, the thermocycling protocol encompasses bringing the contacted sample to a first temperature, then to a second temperature, then to a third and then back to the first temperature at least 15 times, but not more than 50 times.

In some embodiments the method disclosed entails contacting a sample with a composition encompassing a mesylate and thereby forming a contacted sample, subjecting the contacted sample to a thermocycling protocol and thereby forming a cycled sample and subjecting the cycled sample to electrophoretic separation.

Electrophoresis uses the combination of an electrical field with a sieving matrix to separate analytes, such as polynucleotides. With polynucleotides, the phosphate group of each nucleotide unit carries a relatively strong negative charge, much stronger than any charges on the bases. For this reason, the mass-to-charge ratio of the polynucleotides is largely independent of the base composition.

In the presence of an electrical field a DNA molecule that is 10 nucleotides long will experience relatively the same force pulling on as a DNA molecule 100 nucleotides long. Therefore, to separate nucleic acid species based on length electrophoretically requires that the nucleic species be passed through a sieving matrix that retards mobility. The progress of larger species through the matrix is slower than smaller molecules. In this way, smaller species migrate ahead of larger species as electrophoresis proceeds.

An electrophoretic technique is capillary electrophoresis (CE). In CE, a specimen is introduced to an end of a narrow capillary tube filled with a polymer solution. The polymer solution serves as a sieving matrix.

Detection of the separated nucleic acid species in CE is routinely performed by detecting laser induced fluorescence at a fixed position along the capillary. Fluorescently labeled primers are used to amplify the nucleic acid species. Smaller labeled nucleic acid species arrive at the detection point first followed by larger labeled nucleic acid species. By differentially labeling the primers, and in turn the amplified species, multiple loci can be analyzed in the same capillary. The use of different dyes allows even for resolving two different nucleic acid species that migrate at the same rate.

Accordingly, in some embodiments a method is disclosed encompassing contacting a sample with a composition and thereby forming a contacted sample, subjecting the contacted sample to a thermocycling protocol and thereby forming a cycled sample and then subjecting the cycled sample to electrophoretic separation wherein the sample encompasses filter paper suspected of possessing a nucleic acid, the composition encompasses Tris-mesylate (10-50 mM), potassium methanesulfonate (30-80 mM), bovine serum albumin (1.2-4 mg/ml), glycerol (3-8% volume), $MgSO_4$ (1.4-2.4 mM), Sodium Azide (0.01-0.04%), dATP (150-250 mM), dCTP (150-250 mM), dGTP (150-250 mM), dTTP (150-250 mM), a primer pair and a DNA polymerase, the thermocycling protocol encompasses bringing the contacted sample to a first temperature, then to a second temperature and then back to the first temperature at least 15 times, but not more than 50 times and the electrophoretic separation is capillary electrophoresis. In other embodiments, the thermocycling protocol encompasses bringing the contacted sample to a first temperature, then to a second temperature, then to a third and then back to the first temperature at least 15 times, but not more than 50 times.

In some embodiments a method is disclosed encompassing contacting a sample with a composition and thereby forming a contacted sample, subjecting the contacted sample to a thermocycling protocol and thereby forming a cycled sample and then subjecting the cycled sample to electrophoretic separation and thereby detecting the presence or absence of an amplicon. An "amplicon" refers to an amplified polynucleotide sequence; more specifically a polynucleotide sequence resulting from PCR amplification.

EXAMPLES

Mesylate Containing PCR Master Mix Improves Amplicon Recovery in the Presence of Inhibitors Experiments were performed comparing a mesylate containing master mix to a master mix lacking mesylate in the recovery of short tandem repeat loci in the presence of a PCR inhibitor. A PCR mesylate master mix was prepared containing Tris-mesylate (15 mM), 35 mM potassium methanesulfate, 0.02% Sodium Azide, 2.1% Glycerol, 800 mM (dNTP), 0.4% Tween® 20, 4 mg/ml bovine serum albumin and 0.28 U/µl Platinum® Taq. The control master mix contained Tris-mesylate·HCl (15 mM), 35 mM KCl, 1.5 mM MgCl2, 0.02% Sodium Azide, 2.1% Glycerol, 800 mM (dNTP), 0.4% Tween® 20, 4 mg/ml bovine serum albumin and 0.28 U/µl Platinum® Taq. For the PCR, 0.5 ng. human male DNA (clone "007") was used as template. Short tandem repeat loci were amplification targets. The inhibitor used in these experiments was humic acid (300 ng/µl). The reaction volume was 25 µl.

The PCR conditions were: 95° C. for 60 seconds, followed by 29 cycles of (94° C., 10 seconds, 59° C., 90 seconds). After the final extension at 59° C., the reaction was held at 60° C. for 10 minutes and then 4° C.

The presence or absence of amplified short tandem repeat loci was detected by capillary electrophoresis. To each PCR, 0.4 µl GeneScan™ 600 LIZ™ size standard v2.0 and 9.6 µl of Hi-Di™ formamide. After the addition of these reagents, each reaction was vortexed and subjected to centrifugation briefly. The reactions were then heated to 95 oC for 3 minutes, and then placed on ice. After this, the reactions were loaded onto a capillary electrophoresis instrument. The presence or absence of an amplified short tandem repeat locus was determined by detecting fluorescence. One primer of each primer pair used to amplify each short tandem repeat loci was fluorescently labeled.

Figure 2A:
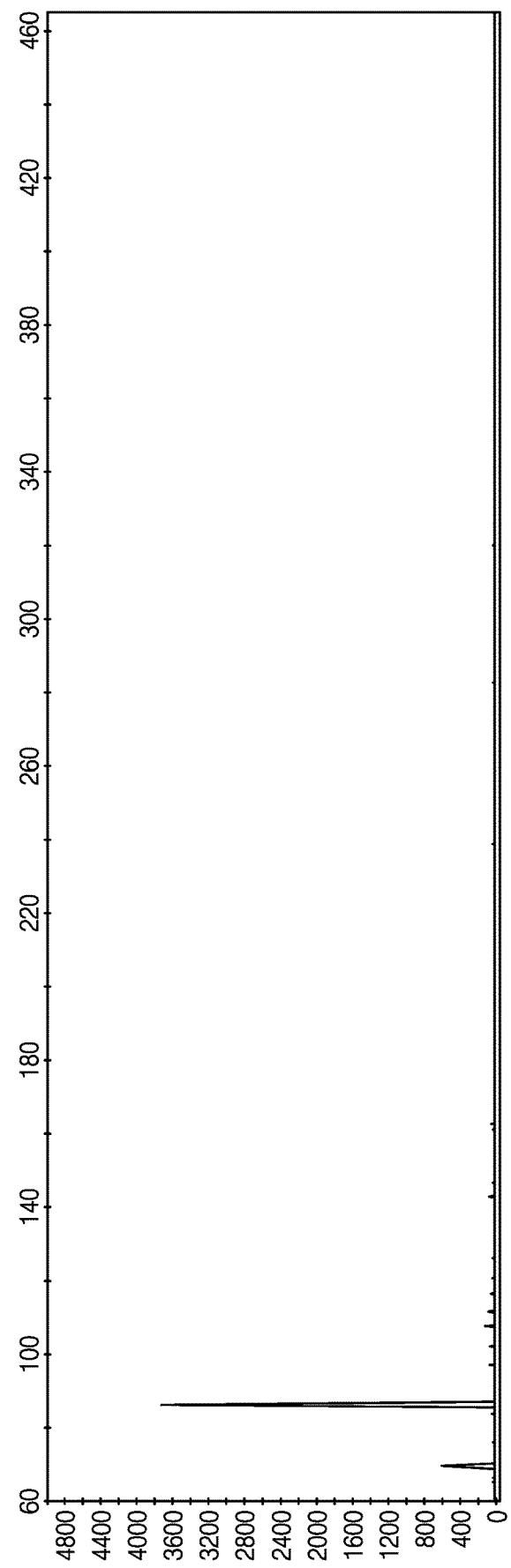
FIGS. 2A and 2B. Electropherograms from capillary electrophoretic separation of amplicons resulting from PCR in the presence of the inhibitor hematin when the sample type is blood. To understand whether a mesylate PCR master mix improved recovery of amplicons was limited to sample type, blood was used as the sample. As observed with purified DNA (Example 1, FIGS. 1A-1J), the number of resolved amplicons is greater when a mesylate is present in the PCR master mix (FIG. 2B) relative to a PCR master mix lacking a mesylate (FIG. 2A).
Figure 2B:
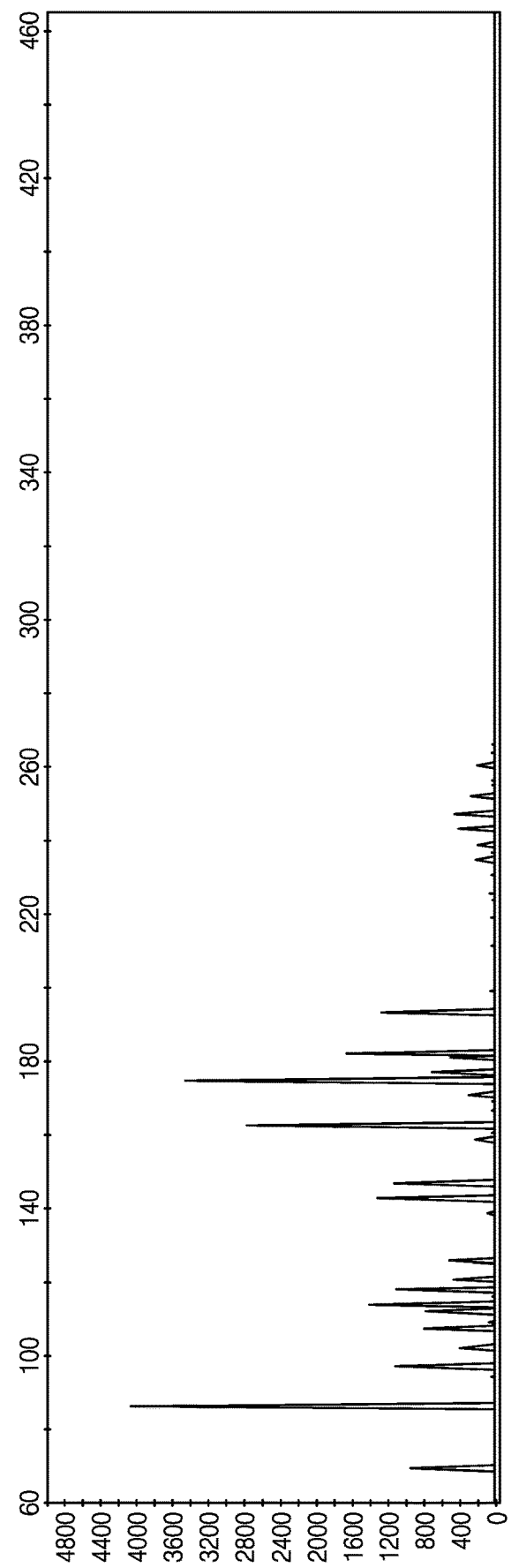

Results from this experimental line is shown on FIG. 1. PCR with a master mix containing mesylate results in significantly more detected short tandem repeat loci relative to a reaction containing a master mix without mesylate.
Mesylate Containing PCR Master Mix Improves Amplicon Recovery from Blood in the Presence of Inhibitors Blood is a common sample type collected during forensic investigations. Whether a mesylate containing master mix would improve amplicon recovery from blood, in the presence of an inhibitor, was tested. The experimental conditions followed are described directly above. The exception being that blood, spotted on FTA® paper, was used as a template source in place of the 007 DNA. Results from this experiment are shown in FIG. 2.

PCR with a master mix containing mesylate results in significantly more detected short tandem repeat loci relative to a reaction containing a master mix without mesylate when the template source is blood.
"Design of Experiments" Testing to Determine the Influence of Master Mix Components and Conditions on Mesylate Master Mix Performance Design of experiments is a systematic method to determine the relationship between factors affecting a process and the output of that process. A number of components and conditions were tested to determine how those factors influenced mesylate master mix performance. These tests included the effect of pH and varying concentrations of potassium methanesulfonate, magnesium methanosulfonate, polysorbate 20, dNTP, bovine serum albumin and Taq polymerase on mesylate master mix performance. Two samples were used for each test. And each test was replicated four times.

Table 2 summarizes an example of such testing; the influence of Taq polymerase, bovine serum albumin and polysorbate 20 were determined by varying the amounts of polymerase activity and percentages of bovine serum albumin and polysorbate 20 in the mesylate master while maintaining other components and conditions of the mesylate master mix fixed.

TABLE 2

| Taq Polymerase | Bovine Serum Albumin | Polysorbate 20 |
|---|---|---|
| 0.2 Units/µl | 2.0 mg/ml | 0 |
| 0.2 Units/µl | 2.0 mg/ml | 0.4% |
| 0.2 Units/µl | 3.0 mg/ml | 0.2% |
| 0.2 Units/µl | 4.0 mg/ml | 0 |
| 0.2 Units/µl | 4.0 mg/ml | 0.4% |
| 0.25 Units/µl | 2.0 mg/ml | 0.2% |
| 0.25 Units/µl | 3.0 mg/ml | 0 |
| 0.25 Units/µl | 3.0 mg/ml | 0.2% |
| 0.25 Units/µl | 3.0 mg/ml | 0.4% |
| 0.25 Units/µl | 4.0 mg/ml | 0.2% |
| 0.3 Units/µl | 2.0 mg/ml | 0 |
| 0.3 Units/µl | 2.0 mg/ml | 0.4% |
| 0.3 Units/µl | 3.0 mg/ml | 0.2% |
| 0.3 Units/µl | 4.0 mg/ml | 0 |
| 0.3 Units/µl | 4.0 mg/ml | 0.4% |

Figure 3A:
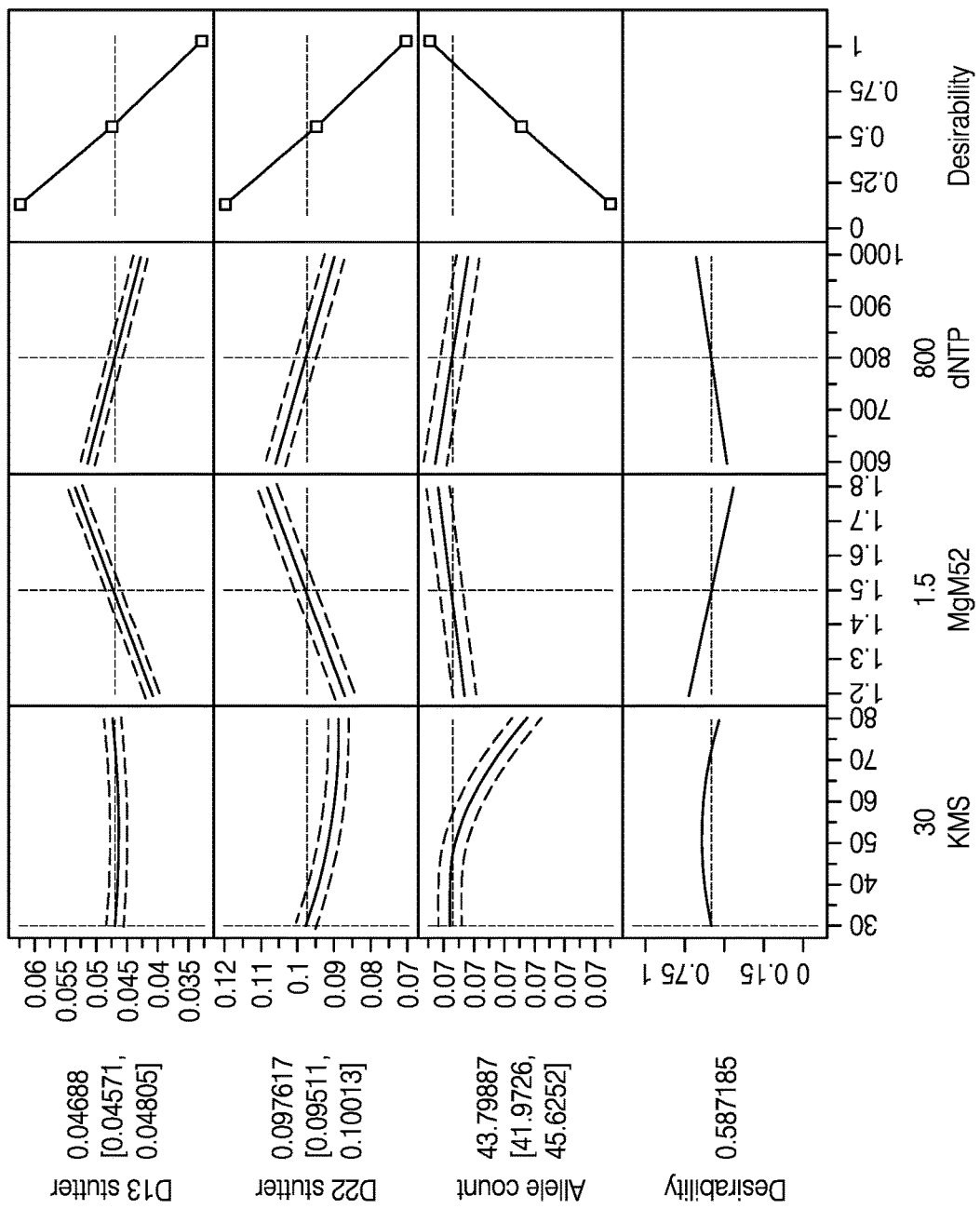
FIGS. 3A and 3B. Summary of results from Design of Experiment testing. Design of Experiment testing is described in the Examples. Briefly, the concentration of a constituent component of the mesylate PCR master mix is varied while other components are not.
Figure 3B:
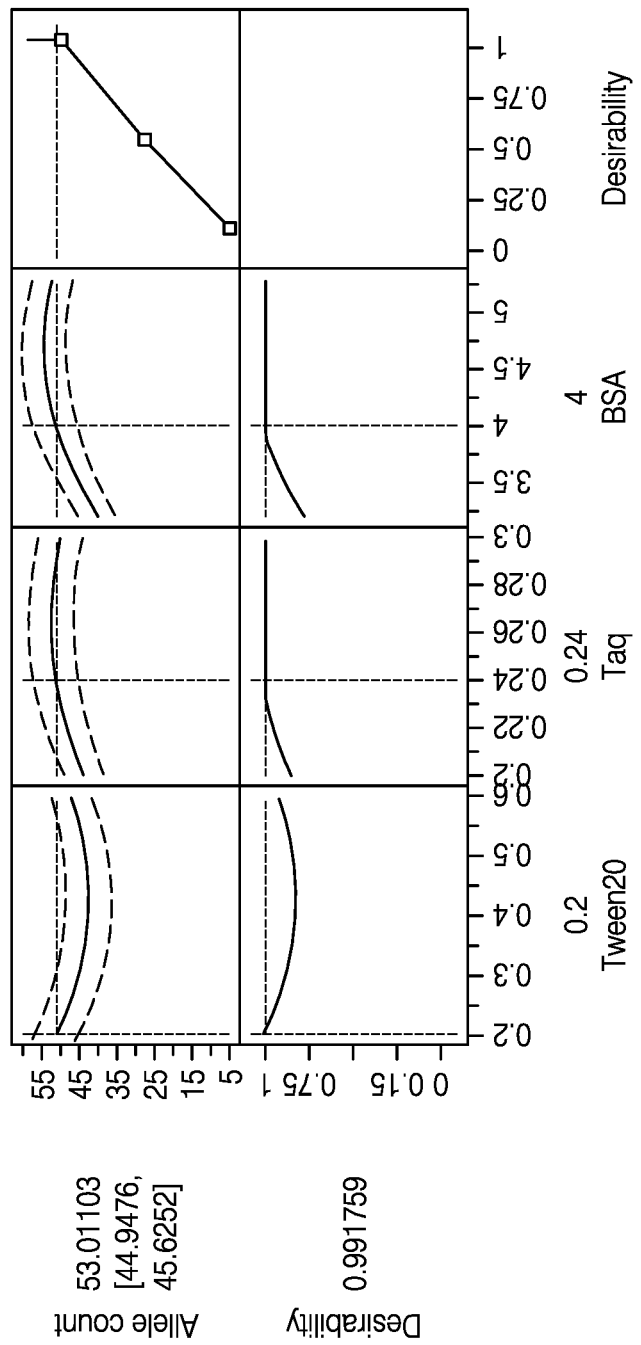

Summary of the data from Design of Experiments testing is shown in FIG. 3

We claim:

1. A PCR master mix comprising:
   Tris-mesylate at a concentration of 10-50 mM;
   potassium methanesulfonate at a concentration of 30-80 mM;
   bovine serum albumin at a concentration of 1.2-4 mg/ml; and
   glycerol at a concentration of 3-8% by volume.

2. The PCR master mix of claim 1, further comprising deoxynucleoside triphosphate.

3. The PCR master mix of claim 1, further comprising a DNA polymerase.

4. The PCR master mix of claim 1, further comprising a deoxynucleoside triphosphate, a non-ionic detergent and a DNA polymerase.

5. A kit comprising a first capped tube comprising a PCR master mix as in claim 1, and a second capped tube comprising a primer.

6. The kit of claim 5, wherein the master mix further comprises a polymerase.

7. The kit of claim 6, further comprising a third capped tube comprising an allelic ladder.

8. A method, the method comprising contacting a sample with a PCR master mix and thereby forming a contacted sample, the PCR master mix comprising Tris-mesylate (10-50 mM), potassium methanesulfonate (30-80 mM), bovine serum albumin (1.2-4 mg/ml), glycerol (3-8% volume), MgSO4 (1.4-2.4 mM), Sodium Azide (0.01-0.04%), dATP, dCTP, dGTP, dTTP, at least two primers and a DNA polymerase, subjecting the contacted sample to a thermocycling protocol, thereby forming a cycled sample and subjecting the cycled sample to an electrophoretic separation and thereby detecting a presence or absence of an amplicon.

9. A PCR master mix comprising one or more of:
   Tris-mesylate at a concentration of 10-50 mM,
   potassium methanesulfonate at a concentration of 30-80 mM, or
   magnesium methanesulfonate at a concentration of 1.2-1.8 mM,
   the PCR master mix further comprising a stabilizer compound, wherein the stabilizer compound comprises glycerol at a concentration of 3-8% by volume.

10. The PCR master mix of claim 9, further comprising a proteinaceous compound.

11. The PCR master mix of claim 10, wherein the proteinaceous compound is bovine serum albumin.

12. The PCR master mix of claim 11, wherein the bovine serum albumin is provided at a concentration of 1.2-4 mg/ml.

13. The PCR master mix of claim 9, further comprising deoxynucleoside triphosphate.

14. The PCR master mix of claim 9, further comprising a DNA polymerase.

15. A PCR master mix comprising one or more of:
Tris-mesylate at a concentration of 10-50 mM,
potassium methanesulfonate at a concentration of 30-80 mM, or
magnesium methanesulfonate at a concentration of 1.2-1.8 mM,
the PCR master mix further comprising a proteinaceous compound, wherein the proteinaceous compound is bovine serum albumin.

16. The PCR master mix of claim 15, further comprising a stabilizer compound.

17. The PCR master mix of claim 16, wherein the stabilizer compound comprises glycerol or sucrose.

18. The PCR master mix of claim 15, wherein the bovine serum albumin is provided at a concentration of 1.2-4 mg/ml.

19. The PCR master mix of claim 15, further comprising deoxynucleoside triphosphate.

20. The PCR master mix of claim 15, further comprising a DNA polymerase.

21. A PCR master mix comprising one or more of:
Tris-mesylate at a concentration of 10-50 mM,
potassium methanesulfonate at a concentration of 30-80 mM, or
magnesium methanesulfonate at a concentration of 1.2-1.8 mM,
the PCR master mix further comprising deoxynucleoside triphosphate.

22. The PCR master mix of claim 21, further comprising a stabilizer compound.

23. The PCR master mix of claim 22, wherein the stabilizer compound comprises glycerol or sucrose.

24. The PCR master mix of claim 21, further comprising a proteinaceous compound.

25. The PCR master mix of claim 24, wherein the proteinaceous compound is bovine serum albumin and wherein the bovine serum albumin is provided at a concentration of 1.2-4 mg/ml.

26. The PCR master mix of claim 21, further comprising a DNA polymerase.

27. A PCR master mix comprising one or more of:
Tris-mesylate at a concentration of 10-50 mM,
potassium methanesulfonate at a concentration of 30-80 mM, or
magnesium methanesulfonate at a concentration of 1.2-1.8 mM,
the PCR master mix further comprising a DNA polymerase.

28. The PCR master mix of claim 27, further comprising a stabilizer compound.

29. The PCR master mix of claim 28, wherein the stabilizer compound comprises glycerol or sucrose.

30. The PCR master mix of claim 27, further comprising a proteinaceous compound.

31. The PCR master mix of claim 30, wherein the proteinaceous compound is bovine serum albumin, and wherein the bovine serum albumin is provided at a concentration of 1.2-4 mg/ml.

\* \* \* \* \*